US006338738B1

United States Patent
Bellotti et al.

(10) Patent No.: US 6,338,738 B1
(45) Date of Patent: Jan. 15, 2002

(54) DEVICE AND METHOD FOR STABILIZING CARDIAC TISSUE

(75) Inventors: Marc Bellotti, Libertyville; Alan W. Marttila, Waukegan; Kenneth J. Steele, Richmond; Scott R. Ariagno, Mundelein; Atif M. Yardimci, Northbrok, all of IL (US); Donald R. Heslington, Orem, UT (US); Charles R. Weyrauch, Salt Lake City, UT (US); Lise J. Herriott, Sandy, UT (US); Donald A. Smith, Wadsworth, IL (US); Cristina J. Stadler, Columbus, IN (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

(21) Appl. No.: 09/386,666

(22) Filed: Aug. 31, 1999

(51) Int. Cl.$^7$ ................................................ A67B 01/00
(52) U.S. Cl. ........................ 606/232; 600/201; 600/210; 600/235
(58) Field of Search ................................ 600/201, 217, 600/226–227, 231, 232, 234, 235, 37, 210; 606/232

(56) References Cited

U.S. PATENT DOCUMENTS

| | | | |
|---|---|---|---|
| 1,382,783 A | 6/1921 | Howard | |
| 1,664,112 A | 3/1928 | Junemann | |
| 2,082,782 A | 6/1937 | Allen | 128/20 |
| 2,608,192 A | 8/1952 | Heitmeyer et al. | 128/20 |
| 2,863,444 A | 12/1958 | Winsten | 128/20 |
| 3,278,207 A | 10/1966 | Barish et al. | 287/12 |
| 3,503,396 A | 3/1970 | Pierie et al. | 128/322 |
| 3,503,398 A | 3/1970 | Fogarty et al. | 128/346 |
| 3,638,973 A | 2/1972 | Poletti | 285/184 |
| 3,858,578 A | 1/1975 | Milo | 128/20 |
| 4,143,652 A | 3/1979 | Meier et al. | 128/20 |

(List continued on next page.)

FOREIGN PATENT DOCUMENTS

| | | | |
|---|---|---|---|
| DE | 3104353 | 12/1981 | |
| DE | 9320139.7 | 12/1993 | |
| DE | 4300307 | 7/1994 | |
| DE | 29707567 | * 8/1997 | 600/231 |

(List continued on next page.)

OTHER PUBLICATIONS

Tea E. Acuff, MD, et al., Minimally Invasive Coronary Artery Bypass Grafting, 1996, Society of Thoracic Surgeins.
Piet W. Boonstra, MD, PhD. et al., Local Immobilization of the Left Anterior Descending Artery for Minimally Invasive Coronary Bypass Grafting, 1997, The Society of Thoracic Surgeons.

(List continued on next page.)

Primary Examiner—Gene Mancene
Assistant Examiner—Michael B. Priddy
(74) Attorney, Agent, or Firm—Lena I. Vinitskaya; John Christopher James; Peter Jon Gluck

(57) ABSTRACT

The present invention is directed to a new and useful device and method for stabilizing cardiac tissue at a surgical site during heart surgery, and specifically useful during beating heart surgery. The device includes a foot for contacting a heart tissue and two arms movably connected together for selective movement to vary and adjust the position of the foot on the heart. The foot and the arm assembly are designed to optimize stability of the foot in contact with heart tissue, and therefore, to optimize stability of the heart during surgical procedure. The device is capable of being mounted on a chest spreader. The foot has a bottom surface which is angled for better stabilization and engagement with the heart.

57 Claims, 10 Drawing Sheets

U.S. PATENT DOCUMENTS

| | | | |
|---|---|---|---|
| 4,492,229 A | 1/1985 | Grunwald | 128/303 |
| 4,616,632 A | 10/1986 | Wigoda | 128/20 |
| 4,635,636 A | 1/1987 | Goldstein | 128/334 |
| 4,655,219 A | 4/1987 | Petruzzi | 128/321 |
| 4,726,356 A | 2/1988 | Santilli et al. | 128/20 |
| 4,854,318 A | 8/1989 | Solem et al. | 128/346 |
| 4,915,333 A | 4/1990 | Bolondi | 248/181 |
| 4,944,741 A | 7/1990 | Hasson | 606/206 |
| 5,002,543 A | 3/1991 | Bradshaw et al. | 606/62 |
| 5,037,428 A | 8/1991 | Picha et al. | 606/155 |
| 5,089,007 A | 2/1992 | Kirsch et al. | 606/205 |
| 5,152,279 A | 10/1992 | Wilk | 128/17 |
| 5,167,223 A | 12/1992 | Koros et al. | 128/20 |
| 5,178,133 A | 1/1993 | Pena | 128/20 |
| 5,195,505 A | 3/1993 | Josefsen | 128/20 |
| 5,195,506 A | 3/1993 | Hulfish | 128/20 |
| 5,195,507 A | 3/1993 | Bilweis | 128/20 |
| 5,224,954 A | 7/1993 | Watts et al. | 606/205 |
| 5,235,966 A | 8/1993 | Jamner | 128/20 |
| 5,267,554 A | 12/1993 | Wilk | 128/20 |
| 5,271,385 A | 12/1993 | Bailey | 128/20 |
| 5,275,608 A | 1/1994 | Forman et al. | 606/170 |
| 5,280,782 A | 1/1994 | Wilk | 128/20 |
| 5,282,826 A | 2/1994 | Quadri | 606/207 |
| 5,284,128 A | 2/1994 | Hart | 128/4 |
| 5,293,863 A | 3/1994 | Zhu et al. | 128/20 |
| 5,308,327 A | 5/1994 | Heaven et al. | 604/96 |
| 5,318,579 A | 6/1994 | Chow | 606/148 |
| 5,339,801 A | 8/1994 | Poloyko et al. | 128/20 |
| 5,339,802 A | 8/1994 | Cook | 128/20 |
| 5,374,277 A | 12/1994 | Hassler | 606/207 |
| 5,381,788 A | 1/1995 | Matula et al. | 128/20 |
| 5,400,773 A | 3/1995 | Zhu et al. | 128/20 |
| 5,431,662 A | 7/1995 | Nicholas | 606/119 |
| 5,447,515 A | 9/1995 | Robicsek | 606/158 |
| 5,452,733 A | 9/1995 | Sterman et al. | 128/898 |
| 5,456,695 A | 10/1995 | Herve Dallemagne | 606/207 |
| 5,474,056 A | 12/1995 | Laborie et al. | 600/214 |
| 5,474,571 A | 12/1995 | Lang | 606/205 |
| 5,476,479 A | 12/1995 | Green et al. | 606/205 |
| 5,507,773 A | 4/1996 | Huitema et al. | 606/207 |
| 5,514,148 A | 5/1996 | Smith, III | 606/151 |
| 5,514,156 A | 5/1996 | Schulze et al. | 606/205 |
| 5,514,157 A | 5/1996 | Nicholas et al. | 606/206 |
| 5,527,319 A | 6/1996 | Green et al. | 606/143 |
| 5,554,101 A | 9/1996 | Matula et al. | 600/214 |
| 5,562,640 A | 10/1996 | McCabe et al. | 604/280 |
| 5,562,700 A | 10/1996 | Huitema et al. | 606/207 |
| 5,571,215 A | 11/1996 | Sterman et al. | 623/66 |
| 5,609,565 A | 3/1997 | Nakamura | 600/229 |
| 5,611,813 A | 3/1997 | Lichtman | 606/205 |
| 5,613,937 A | 3/1997 | Garrison et al. | 600/201 |
| 5,620,458 A | 4/1997 | Green et al. | 606/198 |
| 5,620,459 A | 4/1997 | Lichtman | 606/205 |
| 5,643,178 A | 7/1997 | Moll et al. | 600/204 |
| 5,649,957 A | 7/1997 | Levin | 606/207 |
| 5,656,012 A | 8/1997 | Sienkiewicz | 600/204 |
| 5,690,607 A | 11/1997 | Chin et al. | 600/228 |
| 5,727,569 A | 3/1998 | Benetti et al. | 128/898 |
| 5,730,757 A | 3/1998 | Benetti et al. | 606/198 |
| 5,749,892 A | 5/1998 | Vierra et al. | 600/204 |
| 5,755,660 A | 5/1998 | Tyagi | 600/205 |
| 5,782,746 A | 7/1998 | Wright | 600/37 |
| 5,782,753 A | 7/1998 | DeFonzo et al. | 600/210 |
| 5,795,291 A | 8/1998 | Koros et al. | 600/232 |
| 5,807,243 A | 9/1998 | Vierra et al. | 600/204 |
| 5,820,555 A | 10/1998 | Watkins, III et al. | 600/204 |
| 5,836,311 A | 11/1998 | Borst et al. | 128/897 |
| 5,865,730 A | 2/1999 | Fox et al. | 600/228 |
| 5,875,782 A | 3/1999 | Ferrari et al. | 128/898 |
| 5,894,843 A | 4/1999 | Bentetti et al. | 128/898 |
| 5,921,979 A | 7/1999 | Kovac et al. | 606/1 |
| 5,947,896 A | * 9/1999 | Sherts et al. | 600/229 |
| 5,976,080 A | * 11/1999 | Farascioni | 600/213 |
| 6,007,486 A | * 12/1999 | Hunt et al. | 600/205 |
| 6,007,523 A | * 12/1999 | Mangosong | 604/284 |
| 6,013,027 A | * 1/2000 | Khan et al. | 600/201 |
| 6,036,641 A | * 3/2000 | Taylor et al. | 600/231 |
| 6,050,266 A | * 4/2000 | Benetti et al. | 128/898 |
| 6,071,235 A | * 6/2000 | Furnish et al. | 600/235 |
| 6,102,853 A | * 8/2000 | Scirica et al. | 600/227 |
| 6,102,854 A | * 8/2000 | Cartier et al. | 600/228 |
| 6,132,370 A | * 10/2000 | Furnish et al. | 600/235 |
| 6,213,940 B1 | * 4/2001 | Sherts et al. | 600/231 |
| 6,241,655 B1 | * 6/2001 | Riess | 600/37 |

FOREIGN PATENT DOCUMENTS

| | | |
|---|---|---|
| EP | 0415417 | 3/1991 |
| EP | 0646357 | 4/1995 |
| EP | 0791329 | 8/1997 |
| EP | 0791330 | 8/1997 |
| EP | 0803228 | 10/1997 |
| EP | 0808606 | 11/1997 |
| GB | 2233561 | 1/1991 |
| SU | 736949 | 7/1977 |
| SU | 908343 | 2/1980 |
| SU | 1106488 | 8/1984 |
| SU | 1491436 | 7/1989 |
| WO | 93/08867 | 5/1993 |
| WO | 94/21179 | 9/1994 |
| WO | 95/01757 | 1/1995 |
| WO | 96/16604 | 6/1996 |
| WO | 97/10753 | 3/1997 |
| WO | 97/40738 | 11/1997 |
| WO | 97/40752 | 11/1997 |
| WO | 98/10705 | 3/1998 |
| WO | 98/17182 | 4/1998 |
| WO | 98/27869 | 7/1998 |
| WO | 98/33438 | 8/1998 |
| WO | 98/37814 | 9/1998 |
| WO | 98/41154 | 9/1998 |
| WO | 98/48703 | 11/1998 |
| WO | 98/48704 | 11/1998 |
| WO | 98/49947 | 11/1998 |
| WO | 98/51223 | 11/1998 |

OTHER PUBLICATIONS

Jochen Cremer, MD, et al., Off–Bypass Coronary Bypass Grafting via Minithoracotomy Using Mechanical Epicardial Stabilization, 1997, The Society of Thoracic Surgeons.

Valavanur A. Subramanian, MD, Less Invasive Arterial CABG on a Beating Heart, 1997, The Society of Thoracic Surgeons.

Cornelius Borst, MD, et al., Less invasive coronary artery bypass grafting; without cardiopulmonary bypass and via reduced surgical access, Editorial, Heart 1997; 77:302–303.

Cornelus Borst, MD, et al., Coronary Artery Bypass Grafting Without Cardiopulmonary Bypass and Without Interruption of Native Coronary Flow Using a Novel Anastomosis Site Restraining Device ("Octopus"), May 1996, Vol. 27 pp. 1356–1364, by the American College of Cardiology.

Paul F. Grundeman, MD, PhD, et al., Hemodynamic Changes During Displacement of the Beating Heart by the Utrecht Octopus Method, 1997, 63:S88–91, by The Society of Thoracic Surgeons.

Bruce A. Reitz, MD, Minimally Invasive Cardiac Surgery: Introduction, vol. 9, No. 4 (Oct.) 1997 P. 304, Seminars in Thoracic and Cardiovascular Surgery.

Antonio M. Calafiore, Minimally Invasive Coronary Artery Surgery: The Last Operation, vol. 9 No. 4 (Oct.), 1997, pp. 305–311, Seminars in Thoracic and CArdiovascular Surgery.

Michael J. Mack, MD, et al., Video–Assisted Coronary Bypass Grafting on the Beating Heart, 1997, pp. 63:s 100–3, by The Society of Thoracic Surgeons.

Josef G. Vincent, et al., Coronary Artery Disease; Alternative Surgical Treatment, 1996, vol. 17, abstr suppl, European Heart Journal.

Erik W. L. Jansen, MD, et al., Experimental Off–Pump Grafting of a Circumflex Branch via Sternotomy Using a Suction Device, 1997, pp. s93–96, The Society of thoracic Surgeons.

G. D. Angelini, MD, M.Ch., F.R.C.S., A Simple, Inexpensive Method of Heart Retraction During Coronary Artery Bypass Surgery, Aug. 1998, 46:246–247, Ann Thorac Surg.

John A. Rousou, MD, Cardiac Retractor for Coronary bypass Operations, 1991, 52:877–878, Ann Thorac Surg.

United States Surgical Corp., Cardiovascular Marketing Newsletter, Heart Stabilizer, Nov. 1996.

CarioThoracic Systems, Beating Heart Bypass, A New Approach, 1996, CardioThoracic Systems, Inc.

Shoji Eguchi, "Heart Retractor" used for anastomosis of the circumflex artery in Coronary Artery Bypass Surgery, 1987.

E. Buffolo et al., Direct Myocardial Revascularization without Cardiopulmonary Bypass, Thorac. Cardiovasc. Surgeon 33 (1985) pp. 26–29.

E. Buffolo, et al., Myocardial Revascularization Without Extracorporeal Circulation, European Journal of Cardio–Thoracic Surgery (1990) 4:505–508.

Richard P. Cochran M.D., et al., Bovine Pericardium: A Source of Pulmonary Venous Obstruction in the Mustard Procedure, Ann. Thorac. Surg., Nov. 1987, 44:552–553.

Kirk R. Kanter, M. D., et al., Improved Technique for the Proximal Anastomosis with Free Internal Mammary Artery Grafts, Ann thorac Surg., Nov. 1987, 44:556–557.

Lawrence S. Fox, M.D., An Easy and Safe Technique for Ventricular Septa Defect Closure in Hearts with Atrioventricular Discordant Connection and Dectro cardia, Ann Thorac Surg., Nov. 87, 44:558–559.

Neal L. Eigler, M.D., et al., Improving Detection of Coronary Morphological Features From Digital Angiograms, Effect of Stenosis–Stabilized Display, Nov. 23, 1993.

Enio Buffolo, M.D., et al., Coronary Artery Bypass Grafting without Cardiopulmonary Bypass, 1996 by Society of Thoracic Surgeons.

William J. Fanning, M.D., et al., Reoperative Coronary Artery Bypass Grafting Without Cardiopulmonary Bypass, 1993 by The Society of Thoracic Surgeons.

Albert J. Pfister, M.D., et al. Coronary Artery Bypass Without Cardiopulmonary Bypass, vol. 54, Issue 6, pp. 1085–1092, 1992, Ann Thorac Surg.

John A. Rouson, M.D. et al., Cardiac Retractor for Coronary Bypass Operations, vol. 52, pp. 877–878, 1991, Ann. Thorac Surg.

Frank Bacham, M.D. et al., A Simple Technique for Stabilizing the Heart During Right Coronary Grafting, Mar. 15, 1992, Mercy & Presbyterian Hospital, Charlotte, NC.

James I. Fann, et al. Minimally Invasive Mitral Valve Surgery, vol. 9, No. 4(Oct.) 1997, pp. 320–330, Seminars in Thoracic and Cardiovascular Surgery.

Redmond P. Burke, Minimally Invasive Techniques For Congentail Heart Surgery, vol. 9., No. 4 (Oct.)1997, pp. 337–344, Seminars in Thoracic and Cardiovascular Surgery.

V. I. Kolessou M.D., Mammary artery–coronary artery anastosis as method of treatment for anginapectoris, vol. 54, No. 4, Oct. 19967, pp. 535–544, Journal of Thoracic and Cardiovascular Surgery.

Cornelius Borst, et al., Regional Cardiac Wall Immobilization for Open Chest and Closed Chest Coronary Artery bypass Grafting on the Beating Heart: The 'Octopus' Method, vol. 92, No. 8, pp. 848, Cardio–Thoracic and Vascular Surgery.

Erik W. Jansen, et al., Less Invasive Coronary Artery Bypass Grafting on the Beating Heart: Initial Clinical Experience with the Utrecht 'Octopus' Method for Regional Cardiac Wall Immobilization, Supplement 1, Circulation vol. 94, No. 8, Oct. 15, 1996, Cardio–Thoracic and Vascular Surgery.

* cited by examiner

DEVICE AND METHOD FOR STABILIZING CARDIAC TISSUE

BACKGROUND OF THE INVENTION

The present invention relates to devices to facilitate coronary bypass surgery.

Heart disease is the leading cause of premature death in humans, both male and female. A prevalent form of such disease is the restriction of arteries at the heart that provide blood to the heart. Blood flow is reduced by atherosclerosis or other disease. A common treatment for such restrictions is coronary artery bypass graft (CABG) surgery.

CABG is usually performed by placing the patient on a heart-lung bypass machine (cardiopulmonary bypass, CPB), cutting off the blood supply to the heart, stopping the heart from beating (cardioplegia) and performing the surgery. The bypass machine supplies oxygenated blood to the body during the surgery. The surgeon makes a long incision down the center of the chest and cuts through the sternum to expose the heart area. The patient is then placed on the heart-lung bypass machine for the surgery which itself requires certain surgical steps to do the attachment. This procedure, even though common, involves certain risks because the heart is stopped and must be restarted and the trauma of connecting the patient to the bypass equipment.

Recently, some surgeons have been using a so-called beating heart CABG procedure which is less invasive than the above described procedure. The beating heart procedure permits the elimination of the use of the heart-lung bypass machine and allows that the heart will continue to beat during surgery. To accomplish the beating heart surgery procedure, a small area of the heart at the site of the bypass graft must be maintained in a non-moving condition while the heart may continues to beat and move normally outside of the surgical site. To make a bypass graft, the blockage is located and points in the artery on opposite sides of the blockage are located. The surgeon will graft a length of vein or artery taken from another part of the body to the blocked artery at the two points on opposite sides of the blockage to bypass the blockage. This procedure is known as anastomosis.

There has been some attempts made to provide a device for stabilizing a portion of the heart. Some of the existing devices utilize vacuum suction and some utilize mechanical force to provide stabilization. One surgical device for stabilizing a heart during heart surgery is disclosed in PCT International Publication No. WO 97/40752, published on Nov. 6, 1997 and which is incorporated herein by reference. There is, however, a need for an improved device for stabilization of the heart that is highly adjustable and provides more effective immobilization of the surgical site.

To be effective, the device needs to control movement of the heart at the surgical site, limiting movement, for example, to less than about 2 mm. The device must also provide the surgeon access to the surgical site. Since the surgery may involve several sites on one patient, the device also needs to be easy to adjust in position in a surgical environment.

SUMMARY OF THE INVENTION

Among the several objects and features of the present invention may be noted the provision of a device and a method for stabilizing a localized area of a heart at a surgical site to limit movement of the heart at the site during the surgery, including the beating heart surgery.

One particular object of the present invention is to provide a device which is once positioned and locked in place will have minimal movement, for example, of approximately 2 mm or less.

Another object of the present invention is to provide a series of feet configurations that, once placed, allow for optimal visualization of the anastomosis site.

Yet another object of the present invention is to provide a heart stabilizer that allows a surgeon performing the procedure optimal access to the surgical site.

Still further object of the present invention is to provide a heart stabilizer that naturally opens the artery once an incision is made to assist a surgeon in performing the procedure on the artery.

Still another object of the present invention is to provide a heart stabilizer with a foot having angular wings, suture access areas, tie-downs and a bottom surface texture that optimizes the stability of the foot in contact with heart tissue.

Further objects of the present invention are provision of such a device that is easy to adjust yet can be locked firmly in place; the provision of such a device that has a heart engaging foot, at least one arm, and a locking mechanism that will retain the arm and the foot of the stabilizer in position even when the locking joint is loosened to adjust the position of the heart engaging foot.

Additional objects of the present invention are to provide a device that has a reusable and disposable parts and which is easy to use by a surgeon in beating heart CABG procedures and the provision of such a device that can be used with a variety of chest spreaders.

Yet further object of the invention is the provision of a device that allows for a wide variety of foot mounting positions to accommodate optimal access to arteries in all various surgical sites on the heart.

All other objects and features of the present invention will be apparent from the detailed description of the invention.

In one aspect of the present invention, a foot for use with a heart stabilizing device for engaging a portion of a heart during a medical procedure is provided. The foot of the present invention comprises two laterally spaced apart fingers, said fingers each having an inner edge with said edges defining a surgical site therebetween, each finger having a bottom surface, each said bottom surface having an angled surface portion extending upwardly and away from the inner edge. Preferably, an included angle between the angled surface portions is in the range of between about 110° and about 160° and, even more preferably, in the range of between about 120° and 140°. A bridge is secured to and extends between the fingers adjacent an end of each finger. A mounting post is secured to the bridge and extends therefrom. The foot of the present invention may be used with a variety of known stabilizers, and may be attached, for example, to a support structure consisting of two arms adjustably connected to each other. The foot of the present invention may be disposable or reusable.

In another aspect of the present invention, a stabilizing device is provided that includes a locking mechanism that allows for selective locking of the different parts or elements of the device relative to each other. The locking is such that when the locking mechanism is in a locked position, the elements are fixed relative to each other, but if the locking mechanism is in an unlocked position, the elements of the device are still maintained substantially in position relative to one another until moved by an operator. The locking mechanism of the device of the present invention may have frictional resistance to the relative movement of the elements and such resistance is created by a pre-load. The examplary elements of the surgical device for stabilizing cardiac tissue are a foot and one or more elongate arms.

In one examplary embodiment, such pre-load locking mechanism movably connects two arms of the surgical device of the present invention. The device comprises first and second elongate arms and a joint with said first and second arms mounted thereon for selective multiaxis movement of the first and second arms relative to one another. The device also has lock means with a locked position for selectively locking the first and second arms in a selected position relative to one another, and an unlocked position wherein the joint is operable to maintain the first and second arms substantially in position until moved by an operator.

Alternatively, the described locking mechanism may be used only for a movable connection and selective locking between the foot of the stabilizer and one of the arms of the device. Similarly, the above-mentioned locking mechanism may be used for a movable connection and selective locking between one arm of the device and a chest spreader to which such arm is mounted. If desired, in some embodiments, any two or all three of the above-described elements of the device may use the locking mechanism that allows to maintain the elements substantially in position relative to one another until moved by an operator even when the locking mechanism is in the unlocked position.

In an additional aspect of the present invention, a stabilizing device is provided that uses an arm comprising of two portions: a rigid portion and a flexible articulated portion. The articulated arm of the present invention allows for multi-axis movement, including an axial (or sliding), rotational and pivotal movement of the rigid and the articulated portions that improve adjustability of the device of the present invention. The articulated arm includes a locking mechanism operable to secure the articulated portion in a desired configuration.

Yet in another aspect of the present invention a stabilizing device includes a foot connected to a support structure wherein the support structure includes at least one arm pivotally mounted on a base for connection to a fixed object, such as a chest spreader. Such arm is being pivotally movable on the base in substantially only one plane.

A further aspect of the present of the present invention involves the provision of a method of performing heart surgery. The method includes a step of obtaining a device for isolating and stabilizing cardiac tissue comprising a stabilizing foot having at least two heart engaging bottom surfaces which are inwardly angled relative to each other. Then placing the angled heart engaging bottom surfaces on opposite sides of the surgical site; applying force to the heart through the angled bottom surfaces to stretch and stabilize the portion of the heart at the surgical site; and finally, performing a medical procedure on the cardiac tissue at the surgical site.

Other objects and features will be in part apparent and in part pointed out in the detailed description of the invention.

BRIEF DESCRIPTION OF THE DRAWINGS

Corresponding reference characters indicate corresponding parts throughout the several views of the drawings.

DETAILED DESCRIPTION

Figure 1:
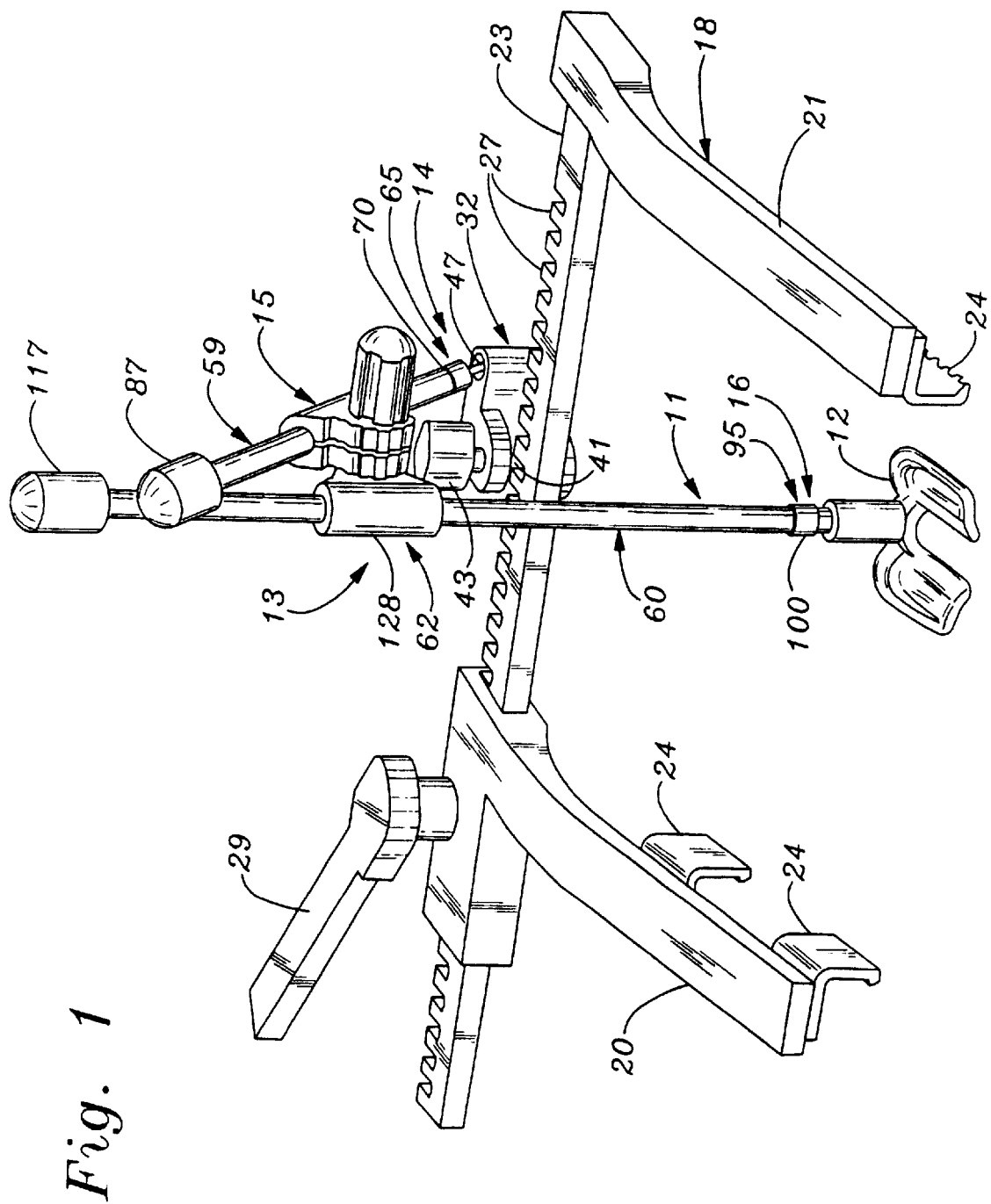
FIG. 1 is a perspective view of one embodiment of a heart stabilizer of the present invention mounted on a chest spreader.

With reference to FIG. 1, a heart stabilizer 11 includes a foot 12 selectively moveably mounted by a support structure 13 on a chest spreader 18. For purpose of identification, one end of the support structure connected to the foot 12 will be called a distal end while the other end of the support structure connected to the chest spreader 18 will be called a proximal end. In use, the foot 12 engages the heart at a surgical site and is held in place by the support structure 13 to reduce movement of the heart at the surgical site while the heart is maintained beating during surgery. In the examplary embodiment of FIG. 1, the support structure 13 includes a pair of arms 59, 60 and first, second and third locking mechanisms 16, 15, 14 respectively. The foot 12, the arm 59 and the arm 60 may be generally called the elements of the heart stabilizer 11. The locking mechanisms 16, 15 and 14 movably connect the elements to each other, for example, the arms 59, 60 to each other, to stabilizer foot 12 and to a chest spreader 18. The support structure may have different configuration, shape and form as long as it allows to achieve placement of the foot 12 at the desired position and orientation at a surgical site. Each locking mechanism 16, 15 and 14 comprises a respective first, second and third joints 95, 62 and 65 shown in more detail in FIGS. 2–4 and described hereinafter. In practice, for example, a surgeon exposes the heart area by opening the patient's chest and holding it open with the chest spreader 18. The stabilizer 11 is then positioned where the foot 12 engages the heart and a force is applied to the heart at the surgical site to hold the site steady while the heart is beating to enable a surgeon to perform the bypass grafting as is known in the art. The force applied to the heart through the foot must be sufficient to withstand the forces supplied by the beating heart and to achieve effective stabilization of the heart.

The spreader 18 can be any suitable spreader as are known in the art. The illustrated spreader 18 includes two spaced apart bars 20, 21 mounted on a support bar which is shown as a rack 23. The bars 20, 21 each have depending hooks 24 secured thereto that will engage portions of the sternum to hold the chest open to provide access to the heart area. Preferably the bar 21 is rigidly mounted on the rack 23 and the bar 20 is moveably mounted on the rack 23. In surgery, the spreader 18 will need to have an adjustable width to accommodate different patient sizes and differing needs for the degree of chest opening sizes. In the examplary form of the spreader shown, adjustability is provided by the rack 23 having a plurality of gear teeth 27 and the bar 20 being provided with a pinion gear (not shown) that is engaged with the teeth. The pinion gear is connected to a handle 29. By rotating the handle 29 about a shaft (not shown) the pinion will rotate and the bar 20 can be selectively moved along the rack 23 to vary the spacing between the bars 20, 21 and the sets of hooks 24 on the bars. As it is understood by those skilled in the art, the spreader shown in FIG. 1 is purely illustrative and any appropriate chest spreader, or retractor, or any other support device suitable for attachment of the stabilizer is within the scope of the present invention.

The support structure 13 is operable for removable securement to or mounting on the spreader 18. In one embodiment, the mounting is accomplished with a base or mounting device 32, as seen in FIG. 1, that can be used on a variety of spreaders to provide more universal adaptation in the use of the stabilizer. In fact, the stabilizer of the present invention was designed with a goal of being capable of attachment to about any spreader available on a market.

Figure 2:
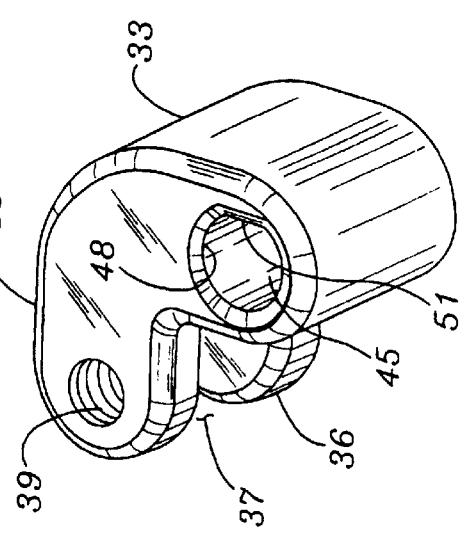
FIG. 2 is a perspective view of a clamp used to mount the stabilizer on a chest spreader.

The mounting device 32 includes a clamp 33 which is best seen in FIG. 2. The clamp 33 includes two spaced apart and generally parallel arms 35, 36 forming a channel 37 therebetween. At least one arm 35, has a through threaded bore 39 opening into the channel 37. A threaded bolt 41, as best seen in FIG. 1, is threaded into the bore 39 and has a distal end (not shown) that will engage the rack 23 to removably secure the clamp 33 to the rack 23. In some embodiments, both arms 35, 36 may have through bores 39. Preferably, the clamp 33 is secured to the rack 23 between the bars 20, 21 and can be positioned at any location therebetween. The bolt 41, as seen in FIG. 1, preferably has a wing head 43 to facilitate tightening and loosening. The clamp 33 is particularly adapted for use on spreaders that have a flat bar to mount to. Other clamp configurations can be used to accommodate other bar shapes. Also, other mounting devices that accomplish releasable engagement of the support structure 13 to the spreader 18 is usable with the present invention.

Figure 3:
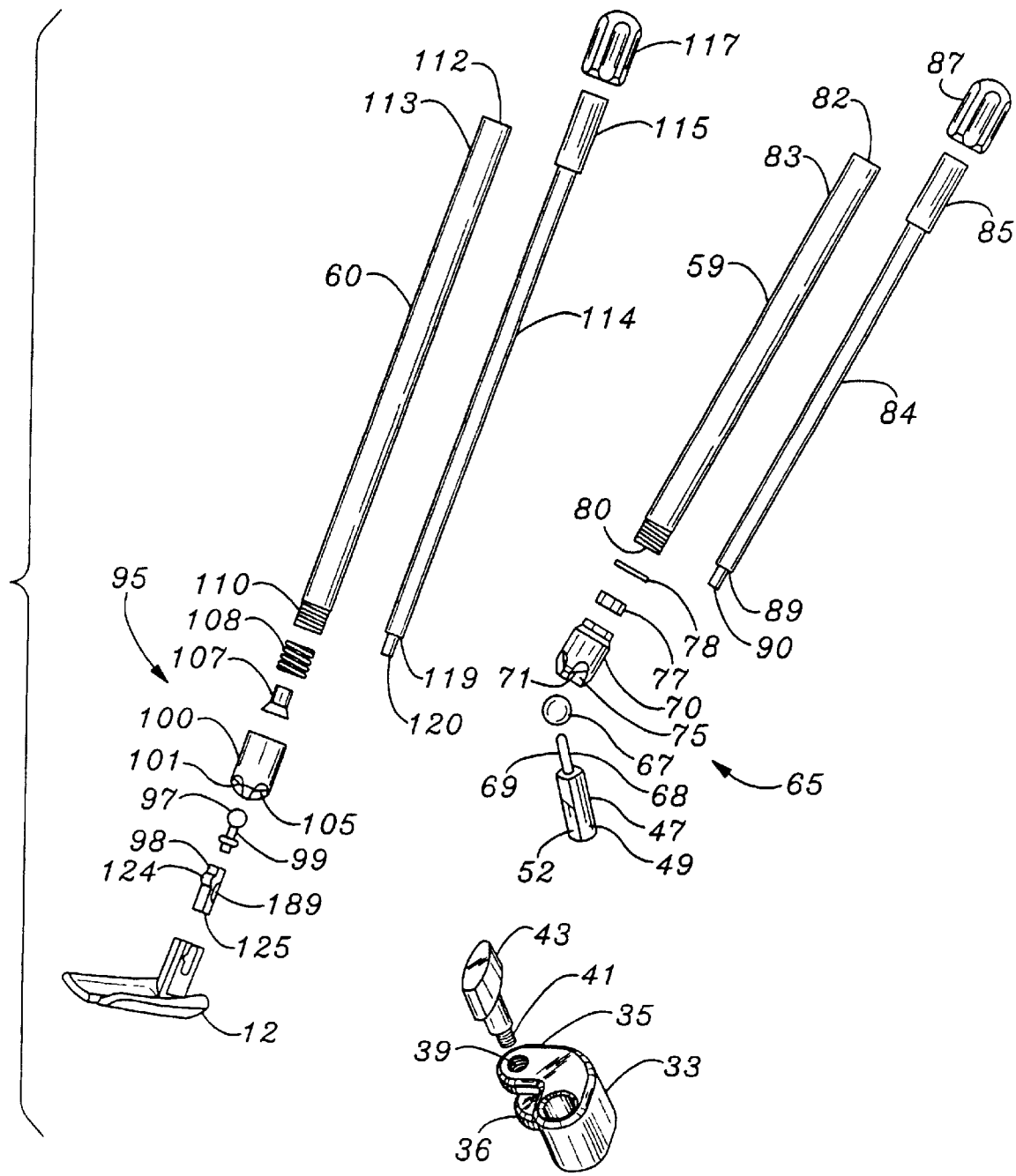
FIG. 3 is an exploded perspective view of the support arms and pivot joints mounted on ends of the arms.

With reference to FIG. 2, the clamp 33 is provided with means for mounting of components of the stabilizer thereon. Preferably the mounting means will permit removable mounting of the stabilizer components. As shown, the clamp 33 has a through bore 45 that may be generally parallel to the bore 39. The bore 45 is adapted to removably receive therein a post 47, as seen in FIGS. 1 and 3, in a manner to prevent rotation of the post in the bore. One convenient way to prevent relative rotation is to have a post 47 and bore 45 with corresponding shapes that are non-uniform in transverse cross section. As shown in FIGS. 2 and 3, the bore 45 and post 47 each have a generally cylindrical portion 48, 49 and a flat portion 51, 52 respectively. The interengagement of the flats 51, 52 will prevent the post 47 from rotating in the bore 45. Means is provided to removably secure the post 47 in the bore 45.

As seen in the embodiment of FIG. 1, the arm 59 of the support structure 13 is preferably movably mounted on the clamp 33 by the locking mechanism 14. In one examplary embodiment, the locking mechanism 14 includes a joint 65, shown in detail in FIG. 3. The illustrated joint 65 permits movement of about 180° of rotation in X and Y axes or planes and up to 360° of rotation about Z plane or axis. The joint 65 allows to move or manipulate the arm 59 quickly and effectively on the clamp 33. One feature of the examplary device of the present invention shown in FIGS. 1 and 3 is that the locking mechanism 14 may include lock means cooperating with the joint 65 to secure it in a selected position when locked and when unlocked the joint 65 will resist relative movement between the arm 59 and the clamp 33 until an operator, e.g. a surgeon, moves the arm 59 relative to the clamp 33. This resistance to relative movement will prevent accidental movement of the support structure 13.

The joint 65 shown in FIG. 3 is a pivot joint. It includes a ball 67 joined to the post 47. The ball 67 can be integral with the post 47 or can be press fitted onto a stake 68 providing a stake portion 69 exposed for a purpose later described. A ball housing 70 forms a ball socket 71 in which the ball 67 is pivotally mounted. A plurality of circumferentially spaced grooves 75 are in a lower portion of the housing 70 and open into the socket 71. The grooves 75 are sized and shaped to receive the stake portion 69 therein to provide for additional pivoting movement of the joint 65.

The examplary joint 65 provides a preload friction between the ball 67 and the ball socket 71 to resist pivoting movement of the ball 67 until urged by an operator. A preload pad 77 is mounted in the ball housing adjacent the ball socket for engagement with the ball 67. The ball 67 is contained between the ball socket 71 and the preload pad 77. Lock means associated with the locking mechanism 14 and joint 65 includes force applying mechanism provided to urge engagement between the ball 67 and the ball socket 71 and preload pad 77. The force applying mechanism is operable to provide a preload friction force when unlocked and an increased friction force when locked by lock means. The force applying mechanism may include, for example, a resilient member 78 such as a preload spring mounted in the ball housing 70 in engagement with the preload pad 77 on the opposite of its engagement with the ball 67. The illustrated resilient member 78 is a beveled disc spring. Any other appropriate mechanism is also within the scope of the present invention. The ball housing 70 is mounted on the arm 59 such as with threaded engagement. As seen in FIG. 6, a lower end 80 of the arm 59 engages the resilient member 78 compressing it a predetermined amount to apply force to the preload pad and thus between the ball socket 71, ball 67 and the preload pad 77. The resulting friction therebetween will resist pivoting movement. The amount of friction can be adjusted by threading the ball housing 70 further onto or off of the arm 59.

The lock means cooperating with the joint 65 includes additional force applying mechanism to lock the joint 65 in place. As shown in FIG. 3, the arm 59 is a tube having a through bore 82 and an upper internally threaded end 83. A rod 84 has an upper externally threaded end 85 that is threadably engaged in the threaded end 83. Thus, rotation of the rod 84 relative to the arm 59 will move the rod 84 axially back and forth within the arm 59. A knob 87 can be threadably mounted on the rod 84 at the threaded end 85 to assist in rotating the rod 84. The rod 84 has an engaging lower end 89 with a reduced diameter tip 90 which is received in an aperture (not shown) in the preload pad 77. By moving the end 89 axially in the direction of the preload pad 77, i.e., a locked position, additional friction is applied between the ball 67, the ball socket 71 and the preload pad 77 to lock the pivot joint against pivoting. Movement of the end 89 axially in a direction away from the preload pad 77, i.e., an unlocked position, will reduce the friction until the preload friction is reached when the end 89 is out of force applying engagement with the preload pad 77. The unlocked position results in the friction force being reduced to as low as or equal to the preload friction and is adequate to prevent accidental pivoting movement of the pivot joint 65, e.g., caused by the weight of the support structure 13 and the foot 12, but not so large as to prevent an operator from adjusting the position of the joint 65.

The examplary locking mechanism 16 of FIG. 1 includes a joint 95 shown in more detail in FIG. 3 and operable for movable mounting of the foot 12 on the arm 60. The locking mechanism 16 and joint 95 with the associated lock means, as seen in FIGS. 1 and 3 may be similar in function and construction to the locking mechanism 14 and joint 65, respectively. Therefore, description of the parts and their functions for the locking mechanism 14 and joint 65 apply to the similar parts of the locking mechanism 16 and joint 95, respectively. The examplary joint 95 may include a ball 97 similar to the ball 67, a stake 98 similar to the stake 68, a ball post portion 99 as an alternative to the stake portion 69, a ball housing 100 similar to the ball housing 70, as also seen in FIG. 1, a ball socket 101 similar to the ball socket 71, grooves 105 similar to the grooves 75, a preload pad 107 similar to the preload pad 77, a resilient member 108 similar to the resilient member 78. The arm 60 also has a lower end 110, similar to the lower end 80, a through bore 112 similar to the through bore 82 and an internally threaded end 113 similar to the internally threaded end 83. A rod 114 is similar to the rod 84, a threaded upper end 115 of the rod 114 is similar to the threaded end 85, a knob 117 is similar to the knob 87 and a lower engaging end 119 with a tip 120 is similar to the end 89 with the tip 90.

The examplary lock means associated with the locking mechanisms 14 and 16 and joints 65 and 95 may be similar and may include the knobs 87, 117, rods 84, 114, preload pads 77, 107, resilient members 78, 108, ball housings 70, 100, elongate arms 59, 60, and balls 67, 97. The preload pads 77, 107 distribute the spring load over a longer surface, prevent metal to metal contact, squeaking and galling.

Further, as seen in FIG. 3, the ball post portion 99 is generally cylindrical and preferably is integral with the ball 97. Like the stake portion 69, it will fit in the grooves 105. The free end can be suitably secured into a bore (not shown) such as by a press fit or gluing in the stake 98 to secure the stake 98 to the ball 97 locking the ball in the ball socket 101. The stake 98 is adapted to be removably mounted to the foot. One examplary manner of the removable attachment of the stake 98 to the foot 12 is described in more detail with reference to FIGS. 5–6 below. In such examplary embodiment the stake 98 may have a transversely extending rib detent 124, as shown in FIG. 3. Also, the stake 98 may be tapered from larger to smaller from the end adjacent the ball 97 toward the distal end 125.

The locking mechanism 16 with the joint 95 and associated lock means may allow for selective locking such that the first joint 95 is operable to be maintained substantially in position even if it is unlocked until moved by an operator. On the other hand, if desired, the locking mechanism 16 may not allow the joint 95 to stay stable when unlocked. Further, if desired, locking mechanism 16 may be different from the locking mechanism 14. For example, locking mechanism 16 may provide for a fixed connection between the foot 12 and the arm 60, such as a snap-fit connection, as described thereafter.

The arms 59, 60 of the stabilizer device may be generally similar in structure and are preferably tubular. It is also preferred that they be made of metal such as aluminum alloy or stainless steel. The arms 59, 60 are preferably round in transverse cross section along a substantial portion of their length so that they can each rotate and move axially in the locking mechanism 15. One exemplary preferred length of the arms 59, 60 is in the range of between about 150 mm and about 230 mm.

Figure 4:
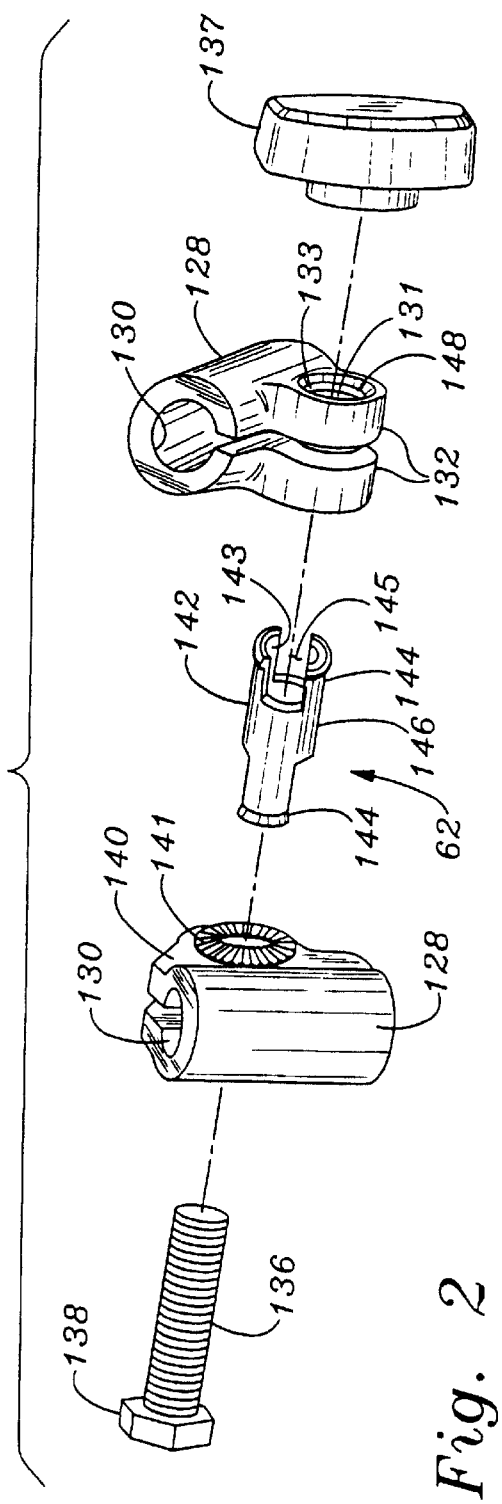
FIG. 4 is an exploded perspective view of C-shaped clamps used in a joint of one embodiment of the stabilizer of the present invention.

As more specifically shown in FIG. 4, the locking mechanism 15 includes a joint 62 that is operable to connect the arms 59, 60 together in movable relation to one another. This locking mechanism allows the arms to slide up and down, therefore, bringing the stabilizer foot 12 closer or further depending on the location and size of the surgical site. Simultaneously, this locking mechanism provides for rotation and selective multi-axis movement of the arms with up to 360° degrees of freedom. Such combined movements provide for a high degree of adjustability of the stabilizer device of the present invention. The locking mechanism 15 also includes an associated lock means. In some embodiments of the present invention, the arms 59, 60 can freely move within the locking mechanism 15 when unlocked and can be retained against free movement in locked in position by adjustment of the lock means. In other preferred embodiments, lock means when locked prevents relative movement of the arms 59, 60 and when unlocked, will still retain the arms in their positions until an operator moves them. In such embodiments, a fixed preload of friction is applied to the arms 59, 60 to substantially retain them in position. There are different ways to apply a fixed preload to the arms 59, 60, some examplary ways are described below.

In the embodiment illustrated in FIG. 4, the examplary joint 62 is a pivot joint and it includes two similar and preferably, identical C type clamps 128. The clamps 128 each have a through bore 130 for receiving therethrough a respective arm 59, 60. An operator can easily move the arms when lock means, hereinafter described, associated with the clamps 128 is in an unlocked position or condition. On the other hand, in some embodiments the through bores 130 may be slightly smaller in diameter than the outside diameter of the respective arm 59, 60 to provide a preload friction force to prevent unintentional movement of an arm in a clamp 128. Alternatively, the preload may be achieved by partially tightening the wing nut 137 as follows. The clamps 128 each have a pair of spaced apart flanges 132 each with a through bore 131. The lock means includes a threaded member, for example, a hex head bolt 136 that extends through the aligned bores 131. A wing nut 137 threadably engages the bolt 136 and when tightened down to a locked position, locks the clamps 128 on the respective arm 59, 60 to prevent their movement. If no preload friction on the arms 59, 60 is provided, tightening of the wing nut 137 can be used to adjust the friction between the arms 59, 60 such that the arms will not freely move in the bores 130.

The bores 131 may have an enlarged portion 133 in one flange 132 with a flat surface (not shown). A head of the bolt 136 may have a plurality of flats 138. One of the flats 138 may engage the flat surface in the enlarged portion 133 to prevent rotation of the bolt when the wing nut 137 is tightened.

As explained, relative movement between the clamps 128 may be controlled when the wing nut 137 is loosened to an unlocked position or condition. The clamps 128 each may have areas that are interengagable with one another to help resist relative motion between the clamps in both the locked and unlocked positions of the bolt 136 and wing nut 137. Such areas can be high friction areas or can have means to achieve mechanical interlocking. As shown in FIG. 4, one of the exterior surfaces 140 may have a plurality of radially extending teeth 141 projecting outwardly from the surfaces 140 for mechanical interlocking. Their interengagement helps prevent relative rotation between the clamps 128. A bushing 142 extends through the aligned bores 131 retaining them in axial alignment. The bushing 142 has a through bore 143 and receives a portion of the bolt 136 therethrough. The bushing 142 has opposite ends each with a laterally projecting collar 144 and longitudinally extending slots 145 in the sidewall 146. The slots 145 permit radial contraction of the sidewall 146 and the collar 144 to permit the collar 144 to pass through the bore 131. The bores 131 also have shoulders 148 that are sized to engage the collars 144 whereby the bushing 142 retains the clamps 128 together and the teeth 141 interengaged. By having the collars 144 spaced appropriately relative to the spacing between the shoulders 148, i.e., slightly less than when unloaded, the diameter of the bores 131 can be adjusted to be maintained slightly smaller than the diameter of the arms 59, 60. Therefore, if desired, the preload friction can be applied to the arms 59, 60 by the clamps 128 to maintain them in a given position when the respective lock means is in the unlocked position, i.e., the wing nut 137 is loosened to an unlocked position, and the teeth can be selectively maintained interengaged. This will prevent relative rotation between the clamps 128, e.g., from the weight of the arm 60 and the foot 12. Moreover, the height of the teeth 141 may be selected such that an operator can effect relative rotation of the clamps 128 when desired if the wing nut 137 is sufficiently loosened. The examplary lock means for the clamps 128, as shown in FIG. 4, includes the bolt 136, wing nut 137, bushing 142 and the teeth 141 and the clamps 128 applying preload friction to the arms 59, 60.

In the illustrated structure, the arms 59, 60 can each move axially and rotationally within the clamps 128 and can move pivotally relative to one another to provide a high degree of adjustability of the device.

Figure 6A:
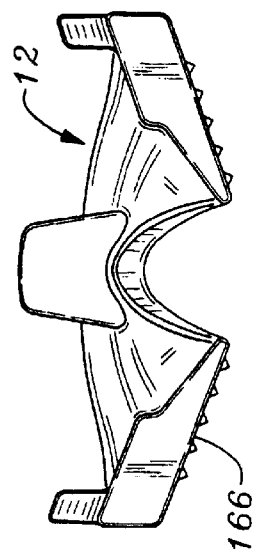
FIG. 6A is an alternative elevation view of the stilizing foot.
Figure 5:
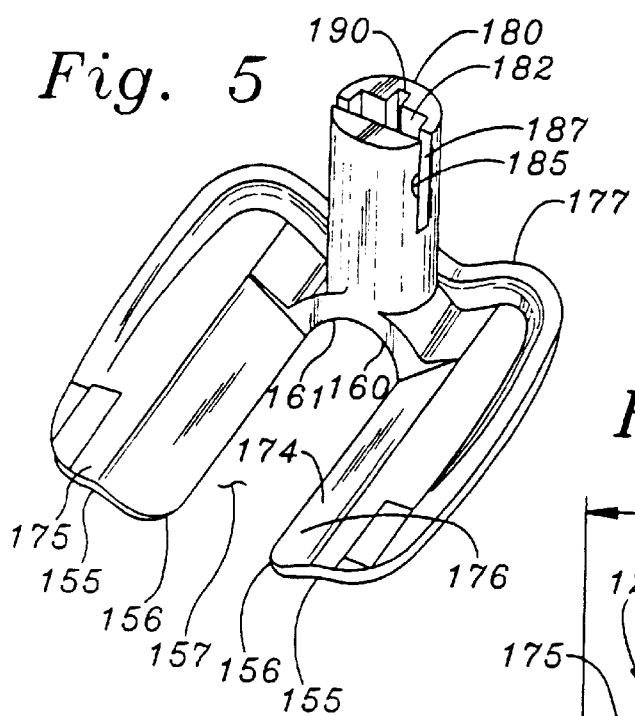
FIG. 5 is a perspective view of a stabilizing foot of the present invention.
Figure 6:
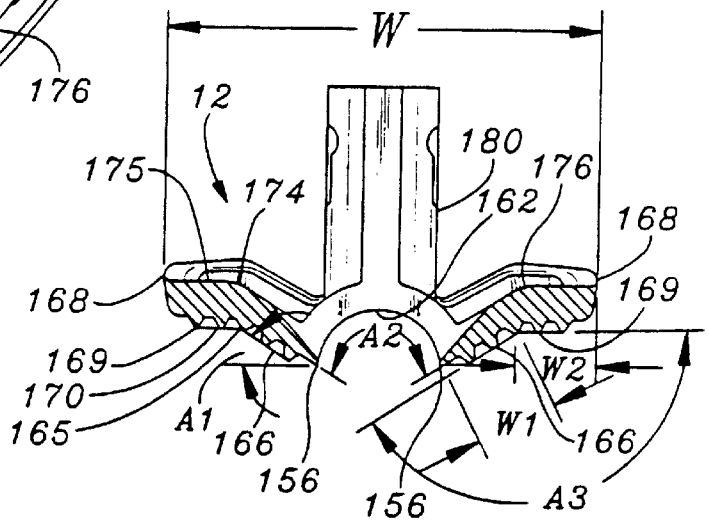
FIG. 6 is a front elevation view of the stabilizing foot.
Figure 7:
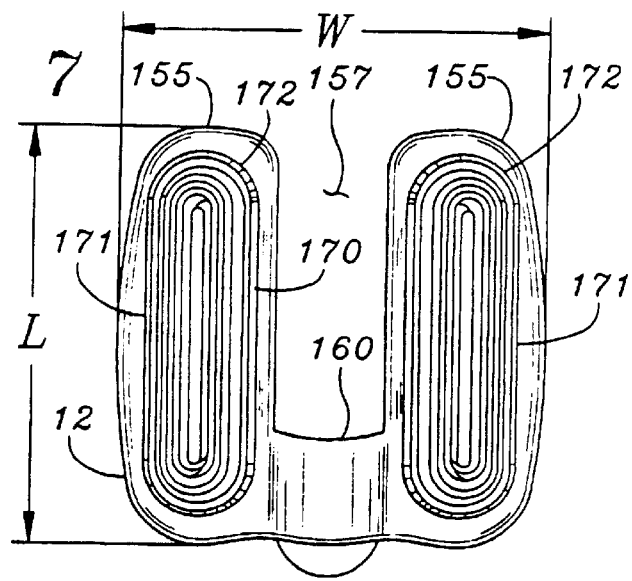
FIG. 7 is a bottom view of the foot.

One preferred embodiment of the stabilizer foot 12 is shown in FIGS. 5–7. The foot 12 is adapted to engage an area of the heart at the surgical site and retain the artery to be grafted onto between two laterally spaced apart fingers or wings 155. The fingers 155 have a bottom surface 165, a top surface 176 and inner edges 156 where the bottom and the top surfaces meet. It is preferred that the edges 156 will form a relatively sharp or acute corner between the bottom surfaces 165 and the top surfaces 176 of the fingers 155. Of course, as it will be understood by those skilled in the art, the edges 156 cannot be so sharp as to damage the tissue of the surgical site when the foot 12 is placed there and the force is applied to the foot. For example, the radius of the corner at the inner edge 156 is about 1 mm and, preferably, about 0.5 mm.

The inner edges 156 are spaced apart along at least a substantial portion of the length of the fingers 155 a distance in the range of between about 6 mm and about 13 mm and preferably in the range of between about 8 mm and about 11 mm. The edges 156 form a slot 157 therebetween so that when the foot 12 is placed on the heart during medical procedure, a surgical cite is disposed in the slot 157.

The fingers 155 have a distal and proximal ends, and they are joined together on one side by a bridge 160 positioned adjacent the proximal end of the fingers 155. Preferably the bridge 160 and the fingers 155 are an integral structure made, for example, of plastic, such as ABS plastic. Therefore, the foot 12 may be disposable. Preferably a bottom surface 161 of the bridge 160 is arcuate and positioned above the inner edges 156 to allow an artery or other vessel in the surgical site to pass thereunder without contact with the bridge 160. The height of the arc of the bottom surface 161 should be sufficient to accommodate the varying sizes of the arteries or other vessels passing thereunder. For example, one preferred height at the peak 162 of the arcuate bottom surface 161 from a plane of the inner edges 156 would be at least about 4 mm.

Each finger 155 has a heart engaging bottom surface 165. It has been found that the shape and size of the bottom surface 165 are important in the operation of the stabilizing device. As illustrated in FIG. 6, the bottom surface 165 includes the beveled or angled surface portion 166 that extends outwardly and upwardly from a respective inner edge 156 or the surgical site slot 157 between the fingers 155. The width W1 of the angled surface portion 166 may vary. For example, in one preferred embodiment, the width W1 is in the range of at least 6mm and preferably in the range of about 7 mm and about 9 mm. The angle A1 of the beveled surface portion 166 from a plane defined by the inner edges 156 is in the range of between about 10° and about 35°, and preferably in the range of between about 10° and about 30°, and more preferably in the range of between about 20° and about 30°. Therefore, the beveled surface portions 166 of the fingers 155 are angled relative to each other (angle A2) in the range of between about 110° and about 160°, and more preferably, in the range between about 120° and about 140°.

The bottom surfaces 165 may also include a second surface portion 169 which extends outwardly from the respective beveled surface portion 166 to a respective outer edge 168 of the foot. A total width W as measured across the outside edges 168 of the fingers 155 may be, for example, in the range of 35 mm to 45 mm. In one preferred embodiment of FIG. 6, each surface 169 is generally parallel to the plane of the inner edges 156 and extends along the length of the fingers. Therefore, in this embodiment an angle A3 between the beveled surface portion 166 and the second surface portion 169 of the fingers 155 will be in the range of about 145°–170°, and more preferably, in the range of about 150°–160°. However, different relative angles between the beveled surface portion and the second surface portion of the fingers 155 are also acceptable.

As an alternative, the bottom surface 165 of the fingers of the foot 12 may have only beveled surface portion 166 and no second surface portion 169, as shown in FIG. 6A. In FIG. 6A the beveled surface portion extends the whole width of the bottom surface. In this embodiment the bottom surfaces of the fingers 155 are angled inwardly relative to each other in the range of between about 110° about 160°, and more preferably, in the range between about 120° about 140°.

Each bottom surface 165 is preferably textured to provide resistance to movement between the heart and the foot 12. One preferred texture is best seen in FIG. 7. The texture includes a plurality of concentric generally oval shaped ribs 170. The ribs 170 have their long dimension, i.e. their long runs 171, running generally along the length of the fingers 155. Also, preferably, the long runs 171 will be generally parallel to the edge 156 and they could be curved or straight. The ribs 170 also have their short runs 172 which run generally transverse to the finger 155, as shown in FIG. 7. The ribs 170 may be, for example, generally triangular with rounded edges in transverse cross-section, or trapezoidal, or circular, or conical, or any other suitable shape and form. Any other appropriate configuration of the texture of the bottom surface of the foot is within the scope of the present invention, including but not limited to ribs, bumps, and indentations of different shapes and forms.

The top surface 176 of the fingers 155 can be of any shape and form. It is preferred, however, that the top surface 176 is shaped similar to the bottom surface having a beveled portion 174 and second surface portion 175, as shown in FIGS. 5–6. The portion 174 of the top surface and the beveled surface portion 166 of the bottom surface meet at the inner edge 156 forming an acute angle (less than 90°). Also, the beveled portion 174 may be substantially parallel to the beveled surface portion 166 along some part of their length, while the surface 174 gradually converges to meet the surface 166 at the inner edge 156. Therefore, the thickness or height of the fingers 155 gradually reduces toward the inner edges 156.

In other embodiments, the top surface 176 may have configuration different from the configuration of the bottom surface 165. In any event, preferably, the top surface 176 should have a compound angle designed to minimize the overall height or thickness of the foot 12, especially in an area of the inner edges 156 of the fingers 155. The combination of the angled bottom surface of the foot with relatively sharp and thin inner edges 156 provides a surgeon with easier access to the surgical site, allows better visualization for the surgeon and achieves significantly more effective stabilization of the heart.

Also, in one preferred embodiment shown in FIGS. 5–6, a post 180 is mounted on the foot 12 to minimize obstruction of access to the surgical site and provide for appropriate orientation relative to various areas of the heart. The post 180 is secured to the bridge 160 and preferably is integral with the bridge 160. The post 180 also serves to connect the foot of the stabilizer to the arm 60, as seen in FIG. 3, and therefore, in some embodiments may be considered as a part of the first locking mechanism 16. Specifically, the below described embodiment of the post 180 provides for a snap-fit locking mechanism between the stabilizing foot and the elongated arm 60 of the stabilizer. The post 180 has a socket 182 that is sized and shaped to releasably retain the stake 98 of the locking mechanism 16 shown in FIG. 3. For example, the socket 182 may include a groove 185 that corresponds to the rib 124 of the stake 98 (FIG. 3) to interengage therewith to snap lock the post 180 and the stake 98 together. To assist the locking and unlocking of the interengagement of the rib 124 and the groove 185, the post has a longitudinal slot 187 that allows the socket 182 to resiliently expand and contract allowing the rib 124 to move along the smaller socket to engage the groove 185. Preferably, the stake 98 and the socket 182 are tapered to provide a tight fit and permit ease of insertion and separation. Also an arrangement of a guide rail 189, shown in FIG. 3, and slot 190, as seen in FIG. 5, is provided to guide the stake 98 into the socket 182 and to help prevent lateral movement of the post 180 relative to the stake 98. The guide rail 189 is part of the stake 98 and the slot 190 is part of the socket 182. Such snap-fit connection of the foot 12 to the arm 60 is preferred. However, in some embodiments of the stabilizer of the present invention other movable connections between the foot and the arm of the stabilizer are appropriate. Such movable connections include, for example, different pivoting mechanism and ball joints. Several of such connections are disclosed in U.S. Pat. Nos. 5,894,843; 5,865,730; 5,807,243 which are all incorporated herein by reference.

The post 180 can be positioned relative to the fingers 155 in several positions or orientations. The desired orientation will be determined according to the area of the heart or another organ that is the surgical site. As best seen in FIG. 5, the post 180 is generally normal to the plane of the inner edges 156 and can be sloped back slightly toward the direction of the rear of the foot 12 to provide more unimpeded access to the surgical site. Additional orientations and locations for the post 180 are shown and described later with reference to FIGS. 11A–E to allow best possible access to anterior and posterior of the heart.

The angled fingers design of the stabilizer foot of the present invention may be used with various devices for heart stabilization known in the art. The angled foot of the present invention may be used on a beating heart or during the CPB surgery. It can be used with mechanical or vacuum stabilizers, such as those disclosed in U.S. Pat. Nos. 5,865,730; 5,891,017 and PCT International publication WO 97/10753, all incorporated herein by reference. The foot of the present invention may also be used with stabilizers attached to the surgical spreader or with a stand-alone stabilizers for use in minimally invasive procedures, such as those disclosed in U.S. Pat. Nos. 5,894,843 and 5,749,892, incorporated herein by reference. Also, the angled foot of the present invention may be reusable or disposable.

Many parts of the stabilizer device, as previously described, may be made of metal, such as stainless steel or aluminum alloy. Some parts, for example, the foot 12, knobs 87, 117, ball housing 70, 100, may be made of plastic. Further, some additional parts, for example, the resilient members 78, 108 may be made of spring steel.

FIGS. 8–12 illustrate different embodiments of heart stabilizer of the present invention. The reference numeral 201 designates generally the stabilizer that is mounted on a chest spreader 18, as previously described.

Figure 8:
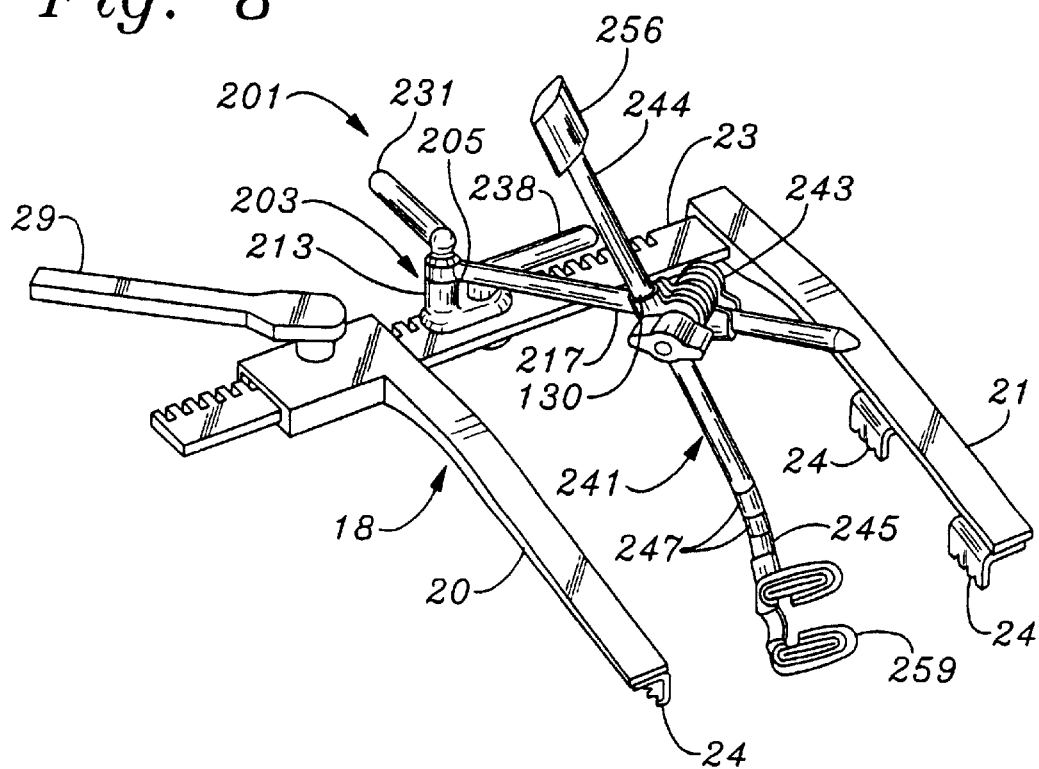
FIG. 8 is a perspective view of another embodiment of the heart stabilizer of the present invention.
Figure 9:
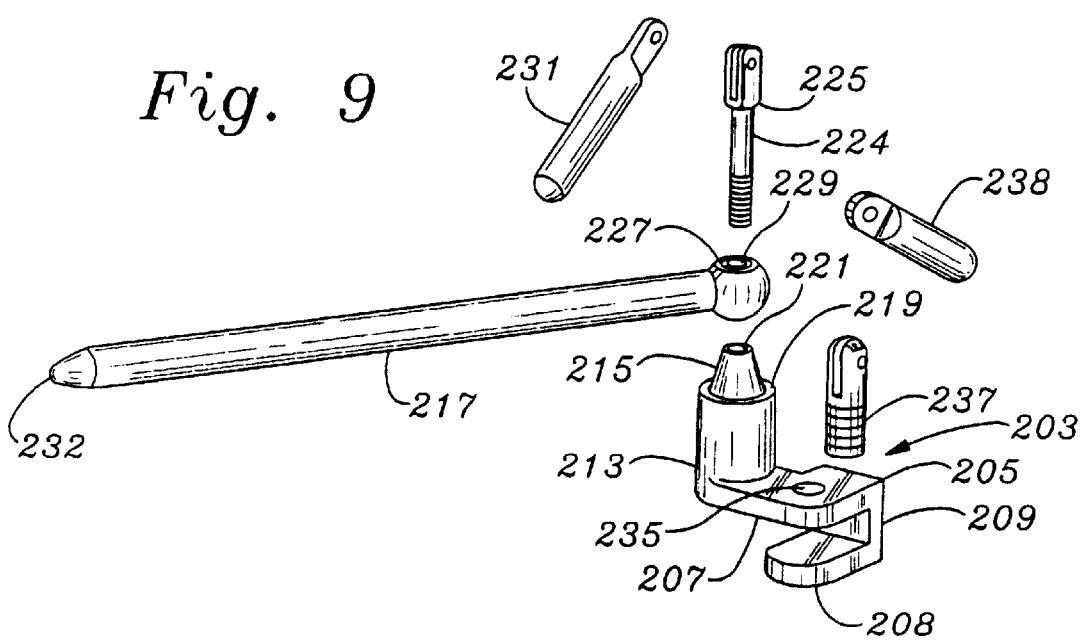
FIG. 9 is an enlarged fragmentary view of the spreader, clamp and intermediate support rod of the stabilizer shown in FIG. 8.

As seen in FIG. 8, the stabilizer 201 includes a base or mounting device designated generally as 203 which includes a clamp 205 for mounting the stabilizer 201 on the spreader 18. As best seen in FIG. 9, the clamp 205 is generally C-shaped having two spaced apart and generally parallel flanges 207, 208 connected together by a section 209. The top flange 207 includes an upstanding post 213, preferably integral with the top flange 207. The post 213 has an axle portion 215 on which a support arm 217 is pivotally mounted. The axle 215 has a reduced diameter relative to the lower portion of the post 213 thereby forming a shoulder 219. The axle 215 is preferably frustoconical. The post 213 has a threaded interior bore 221 opening at the top of the axle 215. A threaded shaft 224 with a shoulder 225 is received in the threaded bore 221 for axial movement therein when rotated.

The arm 217 has a hub 227 with a frustoconical through bore 229 corresponding to the shape and size of the axle 215. The hub 227, and hence the arm 217 is mounted on the axle 215 and is positioned between the two shoulders 219, 225. When the shaft 224 is tightened, the two frustoconical surfaces engage and the arm 217 is clamped for retention in a predetermined position. A toggle handle 231 is pivotally mounted on the shaft 224 and is used to rotate the shaft to tighten the arm 217 on the axle 215 to selectively prevent rotation of the arm about the axle. The handle 231 is preferably pivotally movable to opposite sides of the shaft 224 allowing it to be moved to an out of the way position after tightening. In the described embodiment of the present invention shown in FIG. 9, the arm 217 rotates or moves in only one plane which is preferably generally normal to the axis of the axle 215 and post 213. By being fixed to move in only one plane, the stabilizer 201 is more rigid resulting in less movement of the heart at the surgical site. The plane of motion is within less than about 20° from a general plane of the spreader 18 or a coronal plane of a patient's body, preferably less than about 15° from the coronal plane and most preferably is generally parallel to the coronal plane. The arm 217, except for the hub 227, is preferably solid and is generally round in transverse cross section. The tubular construction of the arm, however, is also acceptable. Preferably, a lead end 232 of the arm 217 may be tapered as shown in FIG. 9 to assist in assembly of the stabilizer 201.

The clamp 205 of the embodiment of FIG. 9 of the present invention further includes a threaded bore 235. A threaded shaft 237 is received in the threaded bore 235 and is axially movable therein when rotated. The free end of the shaft 237 is moved into engagement with the rack 23 (FIG. 8) to releasably fix or retain the clamp 205 in place on the rack. A toggle handle 238 is pivotally mounted on the shaft 237 to help tighten the shaft 237 against the rack 23 and is movable to an out of the way position after tightening.

With reference to FIG. 8, the stabilizer 201 includes two elongate support arms, the previously described support arm 217 and a support arm 241. The support arms 217, 241 are movably connected together with an examplary pivot joint 243. The pivot joint 243 may be similar to the joint 62. The description of the structure of the joint 62 and its functions applies to the pivot joint 243. The arms 217, 241 are received or mounted in the bores 130 like the arms 59, 60 and can independently rotate and move longitudinally or axially in the pivot joint 243. They can also pivot relative to one another.

The arm 241, however, is different from the arm 60 shown in the embodiment of FIG. 1. It has two sections: an elongate rigid section 244 and an articulated section 245. The rigid section 244 is solid, but may be tubular, and preferably is round in transverse cross section. The rigid section is mounted on the pivot joint 243 in a bore 130 and is adapted to mount the arm 241 for both axial and rotational movement in the pivot joint 243 of the stabilizer 201. The rigid section 244 has a knob 256. The articulated section 245 is flexible and consists of a plurality of links 247 movable relative to each other to achieve flexibility of the articulated section 245. The links of the articulated section may be of different shapes and configurations as long as they can effectively move relative to each other to achieve high adjustability of the position of the portion of the arm 241.

Figure 10:
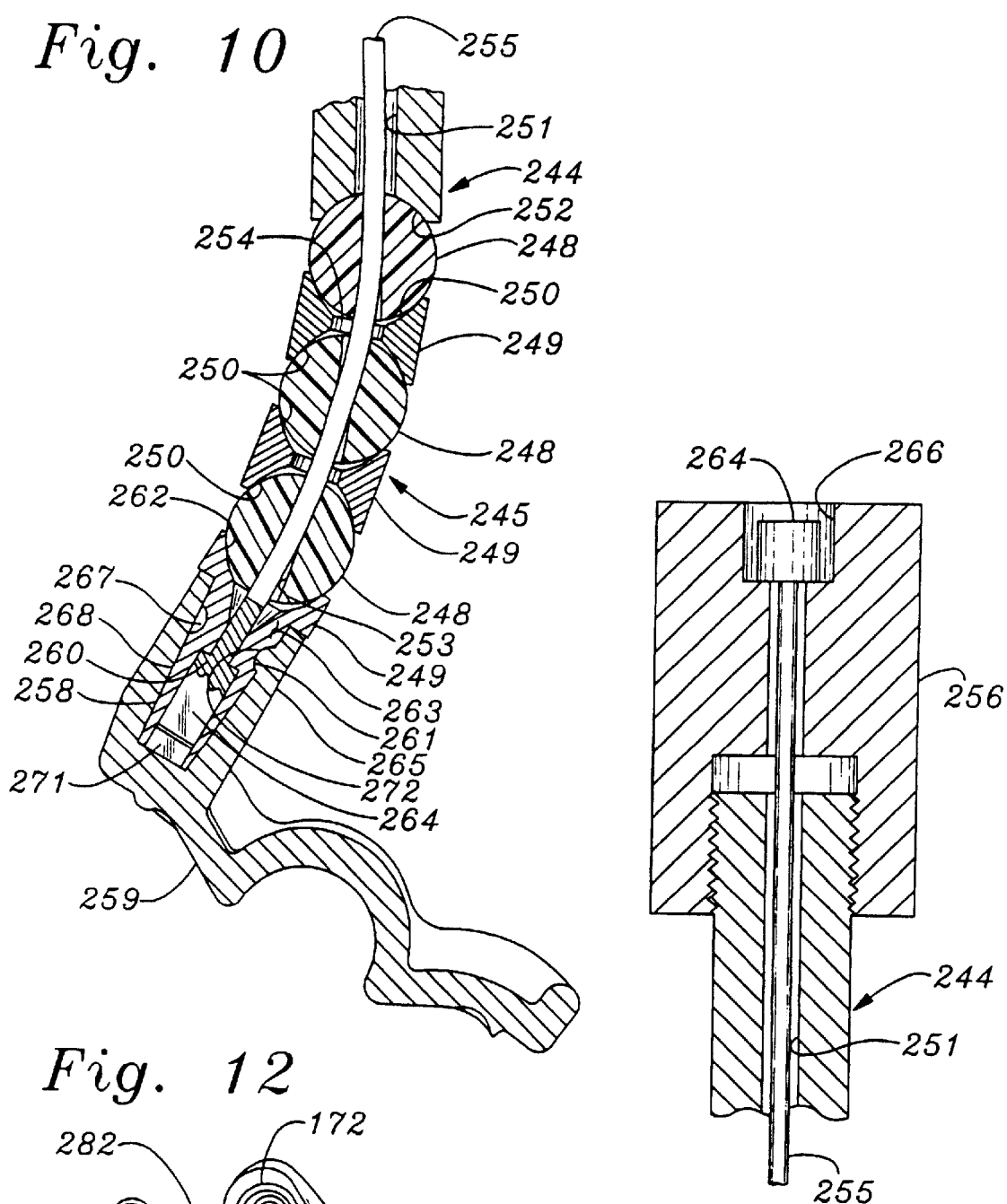
FIG. 10 is an enlarged fragmentary view of a support arm of the stabilizer shown in FIG. 8, the support arm having an articulated end portion.
Figure 12:
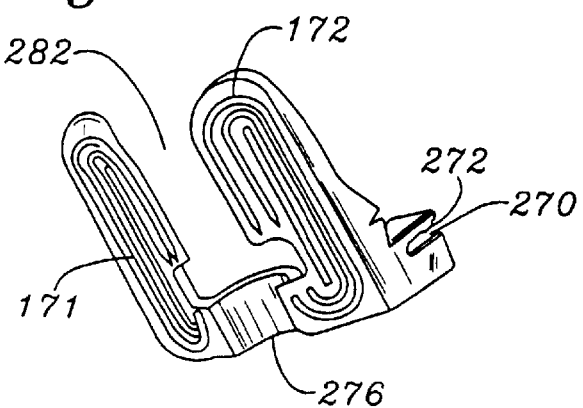
FIG. 12 is a perspective view of the modified foot of FIG. 11B showing a bottom of the foot.

In one examplary embodiment, shown in FIG. 10, the articulated section 245 of the arm 241 includes a plurality of ball and socket links 248, 249 respectively. The socket links 249 have, for example, oppositely facing concave bearing surfaces or sockets 250 that are sized and shaped similar to the exterior surface, which is preferably generally spherical, of the ball links 248. A ball link 248 fits into a socket 250 of an adjacent socket link 249 permitting multi axis movement therebetween. The rigid section 244 of the arm 241 has a socket 252 in one end that receives a ball link 248 therein. The ball and socket links 248, 249 each have a through bore 253, 254 respectively. A cable 255 extends axially through all the ball and socket links 248, 249 through the bores 253, 254 respectively. The cable 255 also extends axially through an interior bore 251 of in the rigid section 244. The cable 255, for example, may have a threaded stud crimped onto its end (not shown) which threads into the clutch (described hereinafter). Alternatively, the cable 255 may be attached to a knob 256 that in turn is threaded onto the rigid section 244 of the arm 241. The knob also may include a set of teeth that will slip relative to the mating teeth in the clutch (not shown) to prevent overtightening of the cable 255. This reduces the risk of breakage making the stabilizer more reliable in operation. The cable 255 may have a cable clamp 264 on both ends. The clamp 264 is preferably cylindrical and fits into a similarly shaped bore 266 in the knob 256 or in the clutch handle (described hereinafter). Rotation of the knob 256 moves it axially along the rigid section 244 and will increase or decrease the cable tension. When the cable 255 is tightened (tension increased), it applies force between the ball links 248 and engaged socket links 249 frictionally retaining them in a fixed orientation. When loosened (tension reduced), the friction is reduced allowing the articulated section 245 to be bent more or less and rotated relative to the rigid section 244 to a desired configuration. In some embodiments, if desired, the ball and socket links 248, 249 can be preloaded for maintaining a minimum amount of friction between the ball links 248 and respective engaged socket links 249, socket 252 and socket 262. The preload friction prevents accidental movement of the foot 259 attached to the arm 241 when the cable 255 is loosened (tension is reduced in the cable 255), but still permits movement of the ball and socket links 248, 249 relative to one another and the rigid section 241. Alternatively, preloading can be accomplished by control of the length and tension of the cable.

Preferably, the length of the articulated section 245 is in the range of between about 30 mm and about 45 mm. Flexibility of the articulated section 245 should permit bending of the articulated section, at least, up to 90° relative to the rigid section 244.

As seen in FIG. 10, the foot 259 is suitably mounted on the distal end of the articulated section 245 in a manner similar to the mounting of the foot 12 described above. A stake 258 is suitably secured to the distal end of the articulated section 245 of the arm. As shown, the stake 258 has a through bore 271 with a shoulder 260. The bore 271 may be shaped like the exterior of the clamp 264 to prevent relative rotation between the cable 255 and the stake 258. For example, in one embodiment, the articulated section 245 may provide for less than about 45° of axial rotation of the distal end and preferably less than about 20° and most preferably less than about 10°.

The clamp 264 has an enlarged end 261 that engages the shoulder 260 to secure the clamp 264 in the stake 258. The stake 258 has a concave socket 262 receiving a ball link 248 therein.

Preferably the stake 258 has an exterior surface that is tapered inwardly toward its free end. The stake 258 fits into a socket 263 in a post 265 for mounting the foot 259 on the arm 241. The post 265 is secured to the foot 259 and is preferably an integral part of the foot. Means is provided to removably retain the stake 258 in the socket 263. The means includes the post 265 with a rib 272 extending across the socket 263. The stake 258 has a grove 267 recessed in each face 268 interengagable with the rib 272.

The slots 270 allow the socket 263 to expand laterally to facilitate movement of the stake 258 into and out of the socket 263. The socket 263 interior is sized and shaped similar to the exterior of the stake 258 for a tight fit with minimal movement between the stake and socket. Preferably, the socket 263 is symmetrical about the slots 270 to allow for the foot 259 to be installed on the stake 258 in different orientations. For example, in some embodiments, the foot 259 may be installed in one of four orientations, 90° of rotation apart. To summarize, in the embodiment of FIGS. 10 and 12, the foot 259 of the stabilizer is nonmovably connected to the lower distal end of the stabilizer arm 241.

FIGS. 11A–11E show various forms and configurations of the foot 259. These feet are similar in construction and the description of one applies to the others except as noted. The difference in the various forms is largely in the position of the post 265 relative to the fingers 274. For example, the post 265 may be located on the bridge 276 or on either of the fingers 274. It can also be oriented in different directions, including parallel, angled and perpendicular directions, to the general plane of the foot as a whole.

Moreover, different embodiments of the foot 259 may additionally include the notches 283, grooves 285 and a different post 265. Each finger 274 includes a notch 283 extending laterally outwardly from the inner edges 280, preferably a distance in the range of between about 5 m and about 7 mm. The edges 280 define a longitudinal slot 282 therebetween. The notches 283 open into the slot 282. The notches 283 facilitate the application of a tourniquet suture to the proximal end of the artery of interest. For example, the foot 259C also includes an upstanding rib 287. The rib 287 contains a plurality of grooves 285, preferably in pairs, that are positioned on opposite sides of the foot 259C, preferably adjacent a respective outside edges 281. The grooves 285 are used by the surgeon to retain a suture that is placed under an artery to lift the artery slightly. The suture holds the artery in position by binding each end of the suture in a respective groove 285. The width of the groove 285 should be small enough that the suture will be frictionally retained in the groove and is preferably enlarged at the top forming a tapered lead in to facilitate inserting the suture in the groove. This suture helps present the artery to the surgeon and helps with stabilization.

The post 265 can have one of several orientations relative to the fingers 274. These different orientations permit the foot 259 to be presented to the heart in several different orientations. It has been found that surgery on the front side of the heart is much easier than the sides or back of the heart. The stabilizer 201 needs to be adapted to engage the heart and stabilize it in locations other than just the front. A particularly difficult artery is the obtuse marginal artery. The heart must be turned up after exposure and the foot 259 has to engage the back side of the heart while the heart is being held up to provide access to the back side.

Figure 11A:
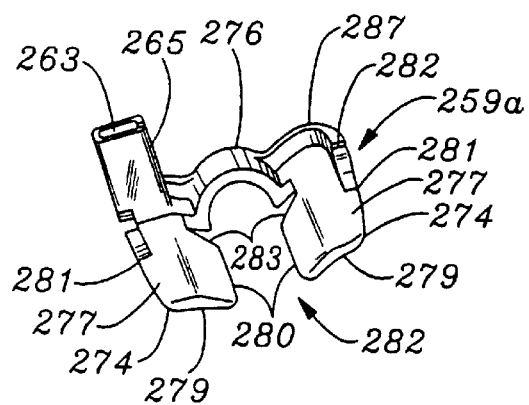
FIGS. 11A, 11B, 11C, 11D, 11E and 11F are perspective views of different embodiments of the stabilizing foot of the present invention.
Figure 11B:
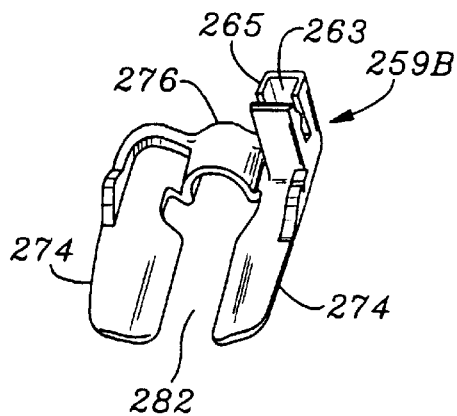
Figure 11C:
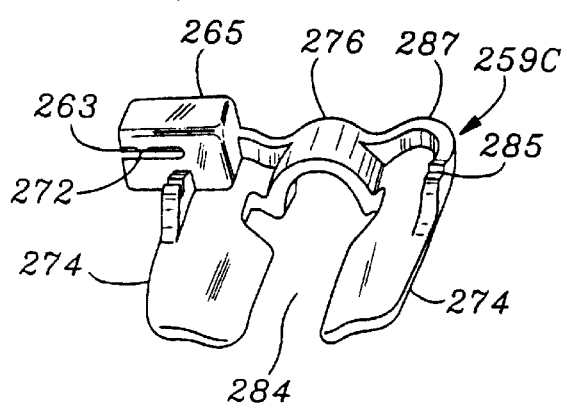
Figure 11D:
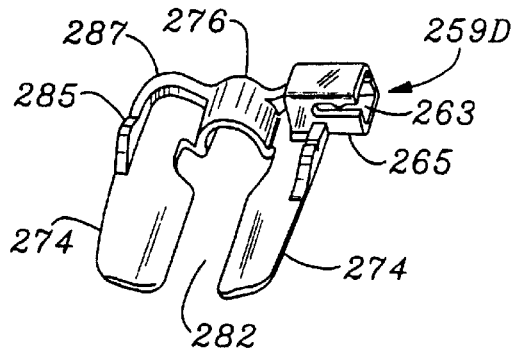
Figure 11E:
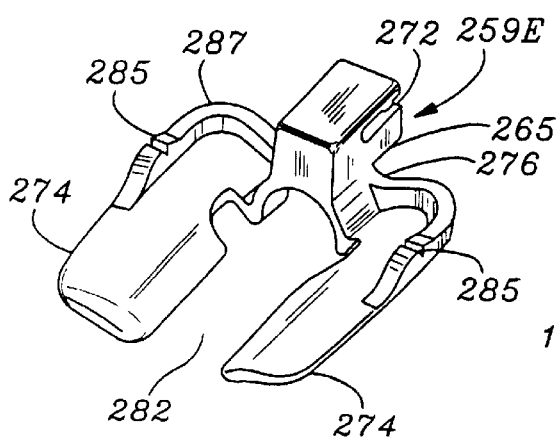

FIG. 11A shows a foot 259A having a post 265 with its longitudinal axis generally normal to the plane of the inner edges 280 and extending from a left finger 274 as viewed from the front of the foot. FIG. 11B shows a foot 259B having a post with its longitudinal axis generally normal to the plane of the inner edges 280 and extending from the right finger 274 as viewed from the front of the foot. FIG. 11C shows a foot 259C having a post with its longitudinal axis generally parallel to the plane of the inner edges 280 and projecting laterally outwardly from the left finger 274. The longitudinal axis of the post in this configuration is generally perpendicular to the longitudinal axis of the inner edges 280 and slot 282. FIG. 11D shows a foot 259D having a post with its longitudinal axis generally parallel to the plane of the foot and projecting laterally outwardly from the right finger 274. The longitudinal axis of the post in this configuration is generally perpendicular to the longitudinal axis of the slot 282. FIG. 11E shows a foot 259E having a post with its longitudinal axis generally parallel to the plane of the inner edges 280 and projecting laterally outwardly from the rear of the fingers 274. The longitudinal axis of the post in this configuration is generally parallel to the longitudinal axis of the slot 282. Also, the longitudinal axis of the post is generally centrally located relative to the slot 282.

These differing orientations of the posts 265 relative to the fingers 274 provide for a wide variety of positions for the foot 259. The adjustability of the arms 217, 241 provides further variety of positions while providing stabilization against movement of the heart at the locus of surgery. It is to be understood that different embodiments of the angled foot 259 can be used on the stabilizer 11 as shown in FIG. 1 or any other known heart stabilizer, as previously discussed.

The components of the stabilizer 201 are preferably made of metal such as stainless steel except for the ball links 248 which are preferably plastic. In operation, the stabilizer 201 should be rigid enough to limit movement of the surgical site between the edges 280 to less than about 1 mm and preferably less than about 0.5 mm.

Figure 11F:
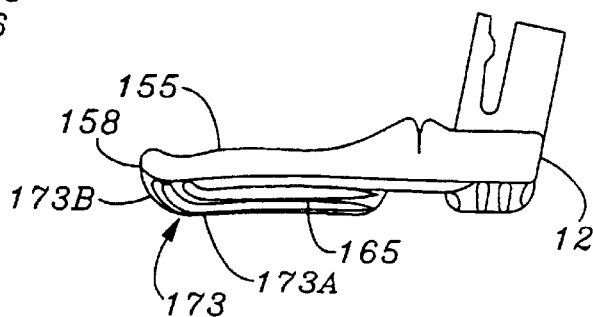

FIG. 11F shows another preferred embodiment of the foot configuration. As seen, the bottom surfaces 165 are contoured along a portion of their length. From the proximal end of the foot 12 adjacent the bridge 160 toward the opposite or distal end 158 of the fingers, the bottom surface 165 is generally planar or slightly curved for a majority of its length. From the distal end 158, the fingers 155 comprise a curved tip 173. The curved section 173 may extend, for example, for about one third of the length of the fingers 155 and it includes two curved portions. From the direction of the bridge toward the distal end of the fingers 155, the bottom surface 165 curves first downwardly forming a first curved section 173A for about one-half of the length of the curved section 173. The curved section 173A is arcuate transverse to the width of the finger 155 and in one example is 0.250 inches long. A second curved section 173B curves upwardly from the curved section 173A toward the distal end of the finger 155. The curved section 173B is also arcuate transverse to the width of the finger 155. The curved sections 173A, 173B together better contour the heart and allow the foot to grip into the heart portion (while pointing down) without damaging it (by having the edge of the distal end pointing up). Such design improves stabilization ability of the device.

Further, in some embodiments, a pad, not shown, may be secured to the bottom surface 165 of the fingers 155. The pad could be used to change the nature of the frictional engagement between the foot 12 and the heart, providing more or less friction. One examplary form of the pad is gauze pad adhesively and removably secured to the bottom 165 of the foot 12 for engagement with the heart. Another examplary pad may be made of a foam, or other material that provides for a friction with the surface of the heart.

Figure 13:
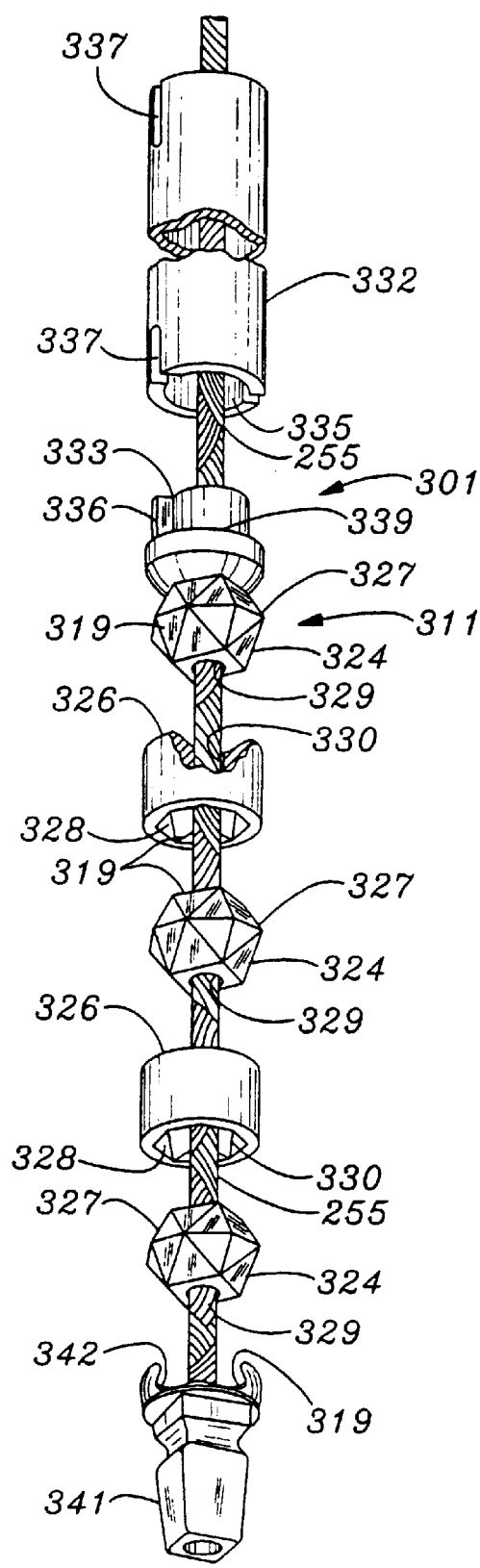
FIG. 13 is an enlarged exploded view of a different embodiment of articulated portion of the support arm with portions broken away to show details.
Figure 14:
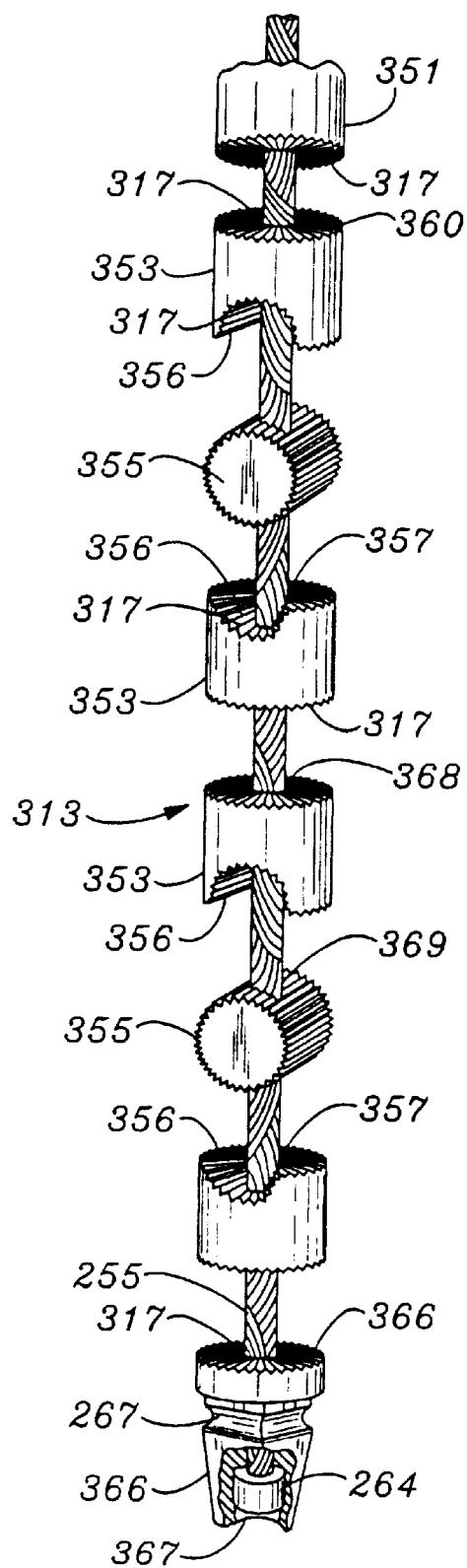
FIGS. 14 and 15 are exploded views of yet other embodiments of the articulated portion of the support arm with portions broken away to show details.
Figure 15:
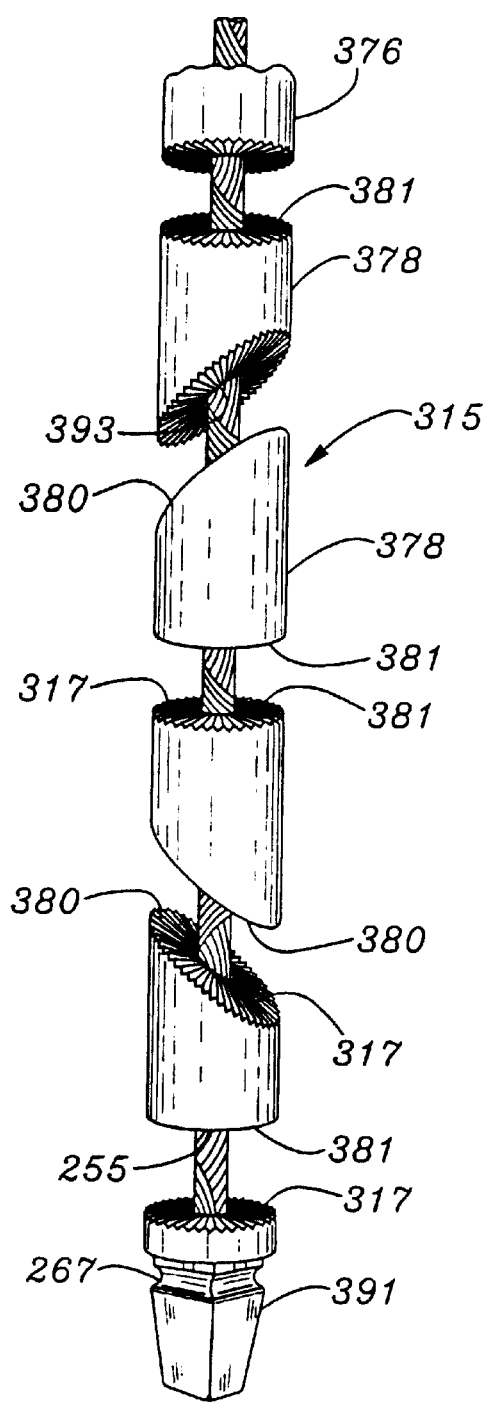

FIGS. 13–15 illustrate different embodiments of the articulated arm 301 of the present invention, which are similar to the arm 241 but with alternative forms of the articulated section 245. The modified arms 301 are usable in the stabilizer 11 or 201, described above. The modified articulated arms 301, each have an articulated section 311, 313, 315 respectively with a plurality of interengageable elements or links retained in interengagement and in superposed relation for example, by the cable 255. Each link is characterized by having a textured surface as hereinafter described that engages with a similarly textured surface to resist relative movement between engaged or mated links. The texture permits reducing the tension required in the cable to maintain the links in a fixed relation to one another. Relative movement between the various links permits bending of the articulated sections 311, 313, 315 for positioning of a foot 12. The texture can take any suitable form such as teeth 317, facets 319, or may utilize a camming action between mating links to separate the links sufficiently to permit relative movement therebetween. Smooth mating surfaces do not require relative axial movement of the mating links to change the angular orientation between links. The surface texture can take several forms as described below. As seen in FIG. 13, the texture includes a plurality of facets that are in the form of adjacent generally flat surfaces. In FIG. 14, the texture takes the form of teeth 317, like gear teeth. To effect relative movement between mating links, i.e., disengage the interengagement of texture elements, e.g. a facet 319 with a facet and a tooth 317 with a tooth, requires either a reduction in the tension of the cable 255, stretching of the cable or both. The texture elements of one link then engage other texture elements of a mating link to assist in retaining the articulated section 311, 313, 315 in a new or desired configuration.

The arms 301 include elongate rigid sections 332, 351, 376 respectively. The rigid sections 332, 351, 376 are similar to each other and to the rigid section 244. They are generally round in transverse cross section, have a generally uniform cross section along a substantial portion of their length, which cross-section is generally round and are tubular with through bores.

FIG. 13 shows an articulated section 311 of the arm 301 which utilizes a plurality of mating links 324 and 326. The links 324 have faceted exterior surfaces 327 and through bores 329 through which the cable 255 extends. The link 324 most adjacent the rigid arm section 332 includes a keyed shank 333 that is receivable in the open end 335 of the rigid arm section 332. Keys 336 fit into grooves 337 opening onto the free end 335 of the rigid section 332 to prevent relative rotation between the shank 333, and hence, the link 324 connected to it. Preferably, the shank 333 and top link 324 are an integral structure. The shank 333 has a shoulder 339 which engages the free end 335 to limit movement of the shank into the rigid section 332. As shown, a plurality of mating links 326 are provided, each having oppositely facing generally arcuate concave surfaces 328 and through bores 330 therein. The surfaces 328 have facets 319 thereon. The links 324 and links 326 are in superposed relation and held together by the cable 255. The facets 319 of the links 324, 326 may have different sizes, shapes and configurations which are all within the scope of the present invention. In the example of FIG. 13, the facets 319 are shown as being triangular. The facets 319, however, can be hexagonal, pentagonal, square, oval and others. Another variation of texturing will include dimples in one of the surfaces 327, 328 and corresponding protuberances on the other surface 327, 328. Any other mating surfaces and textures are within the scope of the present invention. The interengagement of the facets 319 on a link 324 with facets 319 in a mating link 326 provide a more positive lock of the angular position or contour of the curvature of the articulated section 311. The articulated section 311 of the arm 301 also includes a stake 341 that fits into the foot socket 263. The stake 341 is secured to the cable 255 via a cable clamp 264 as shown in FIG. 10 which is crimped or otherwise attached to the free end of the cable 255. The upper end of the stake 341 includes a concave socket 342 that has facets 319 for interengagement with the facets 319 on the link 324. The stake 341 together with the corresponding groove of the post of the stabilizing foot form locking mechanism connecting the stabilizing foot to the articulated section of the arm. The stake 341 may have different configurations and shapes as long as it is capable of interengagement, for example, a snap-fit connection, with the foot 12.

FIG. 14 illustrates another embodiment of the articulated section 313 of the arm of the stabilizer of the present invention. The articulated section 313 is comprised of a plurality of interengaged elements or links including a plurality of socket links 353 and a plurality of axle links 355. As shown, the socket links 353 each have a curved surface 356 forming a transversely extending channel 357 on one end that is textured with ribs or teeth 317 extending transversely of the longitudinal axis of the socket link 353 and generally longitudinally of the channel 357. In the embodiment of FIG. 14 the surface 356 is an arc of a circle of, for example, about 180°. Other angles or configurations are also possible. The other end 360 of the socket link 353 is shown as generally planar with a plurality of radially projecting teeth 317. In the embodiment shown, the end 360 is generally normal to the longitudinal surface of the socket link 353. Other configurations, however, are also within the scope of the present invention. The radially projecting teeth 317 for the top socket engage with corresponding radially extending teeth 317 in the end of the rigid rod section 351 of the arm. As shown, the lower disposed socket link 353 engages a stake 364 having corresponding radially projecting teeth 317 on its free end 366. The articulated section 313 of the arm may include a pair of socket links 353 at the center each having radially projecting teeth 317 on their ends which interengage when the centrally located socket links 353 are mated. The socket links 353 and axle links 355 each have a through bore 368, 369 respectively for receiving the cable 255 therethrough. The articulated section 313 may also have the stake 364 mounted thereon with a through bore 367 for receiving the cable 255 and has a bore portion to receive a cable clamp 264 therein to secure the socket and axle links 353, 355 together and on the rigid section 351 of the articulated arm. When the cable 255 is tensioned, the socket and axle links 353, 355 resist relative movement locking the articulated section 313 in the desired configuration like the articulated sections 245 and 311.

FIG. 15 shows another embodiment of the articulated section 315 of the articulated arm of the stabilizer of the present invention. This embodiment also includes means for securing the articulated section in a desired configuration similar to the means described in the form of invention shown in FIGS. 13 and 14. The articulated section 315 as shown includes a plurality of elements or links 378 with interengageable surfaces that mate with one another. The examplary links 378 as shown are generally round in transverse cross-section and are rod segments having opposite ends 380, 381. The end 381 of each link 378 may be generally perpendicular to the longitudinal axis of the link 378 and the other end 381 may be beveled at an angle from the longitudinal axis of the link. Any desired angle is appropriate. One preferred angle, for example, is in the range from about 20° to about 75° and more preferably is about 45°. The links 378 may be the same or different and they can have different bevel angles on the beveled ends 381. It is preferred that the beveled ends 381 of mating links 378 have complementary bevel angles i.e. their sum equals about 90°. End surfaces 380 may also be beveled in some embodiments. Both end surfaces 380, 381 may be textured which is shown in the form of generally radially projecting teeth 317. The teeth 317 of one surface will interengage with the teeth 317 of the mating surface to provide selective resistance to relative rotation about the longitudinal axes of the links 378.

As shown in examplary embodiment of FIG. 15, the first and second links 378 may interengage on beveled ends 380 while the second and third links 378 may be mated at a generally perpendicular surface 381 and the third and fourth links 378 may be again mated at beveled ends 380. The end 381 of the last link 378 mates with a mating end of a stake 391 similar to the stake 364 shown in FIG. 14 or other described embodiments. Both the stake 391 and the mating surface of the last link 378 may have textured surfaces for better interengagement. Each of the links 378 has a through bore 393 through which the cable 255 extends. The cable 255 connects the stake and the links 378 to the rigid section 376 of the arm. The articulated section 315 operates similar to the articulated sections 245, 311, 313 and may be similarly retained in a desired configuration by cable tension and a clamp 264.

To move the exemplary links 324, 326, 353, 355, 378 relative to one another and shape the configuration of the respective articulated section 311, 313, 315, the tension in the cable 255 needs to be reduced from a locking tension to allow for easy relative movement between adjacent links. The cable 255 is tensioned to secure the articulated sections 311, 313, 315 in the desired configuration. Because of the interengaged textured surfaces, the tensile strength of the cable 255 can be reduced, relative to cable strength for articulated sections that do not utilize textured mating surfaces, while still providing adequate rigidity in the articulated sections 311, 313, 315. The articulated sections 311, 313, 315 have the same degree of freedom of movement as that described for the articulated section 245. The present invention is not limited to the provided examples of the links of the articulated portion of the arm of the heart stabilizer. Any other shapes, forms and configurations of the links and their interengagement that provide flexibility to the portion of the arm of the stabilizer are within the scope of the present invention.

Figure 16A:
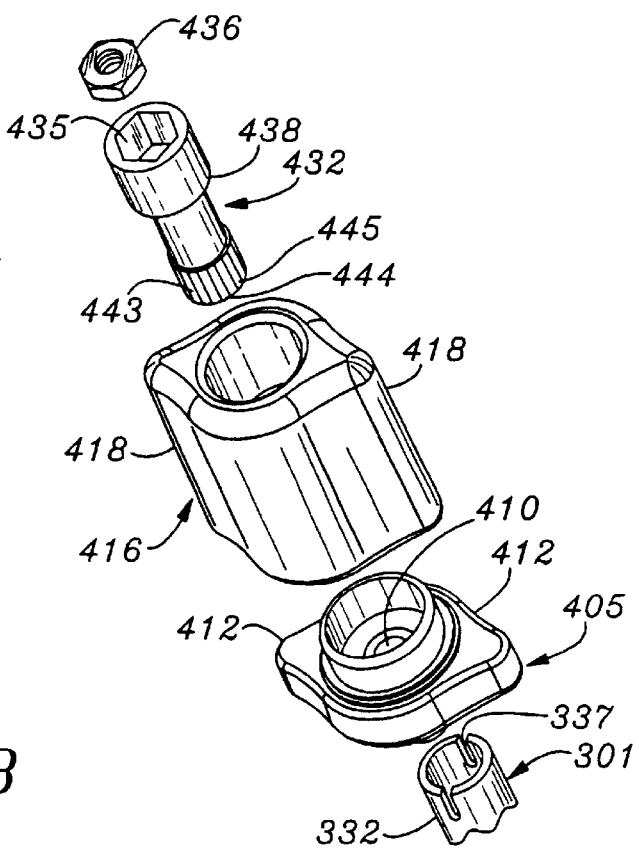
FIG. 16A is an exploded perspective view of an examplary clutch for use with the stabilizer of the present invention.
Figure 16B:
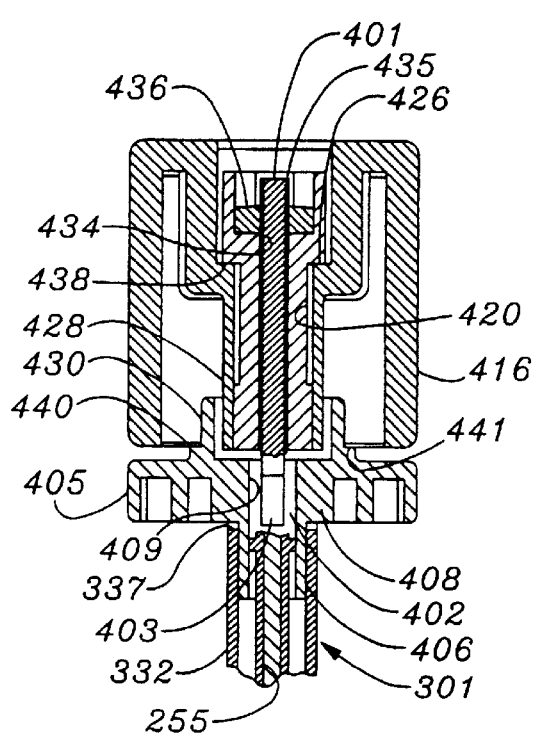
FIG. 16B is a cross-sectional view of the clutch of FIG. 16A.
Figure 16C:
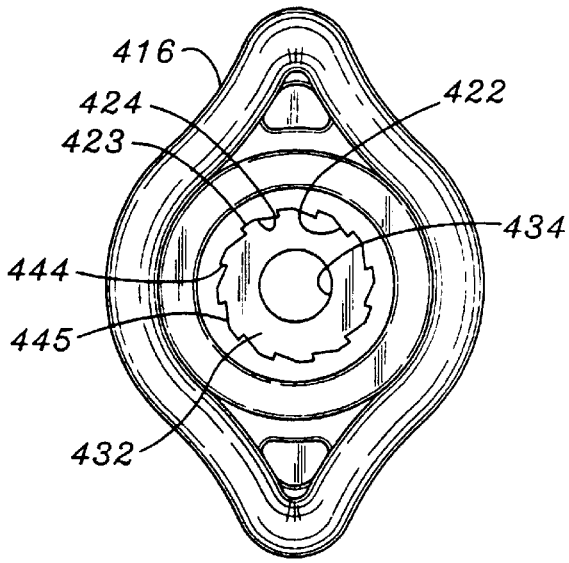
FIG. 16C is a top view of a handle of the clutch of FIG. 16A.

With reference to FIGS. 16A–C, the arms 301, 305, 309 are provided with means to tension the cable 255. The means preferably includes a clutch to prevent over tensioning of the cable. It is to be understood that the arm 241 can be similarly provided with such means for tensioning the cable. The clutch tightening means is best seen in FIG. 16A–C showing it in relation to the arm 301 but it can be used on the other articulated arms. With reference to FIG. 16B, a threaded shank 401 is secured to the cable 255 such as by crimping. The shank 401 also has a cylindrical collar 402 with one or more flats 403. A first handle 405 as seen in FIG. 16A,B, has a shaft 406 receiving the free end of the rigid section 332 of the arm 301. The handle 405 may have keys 408 that fit in the grooves 337 on the rigid section 332 of the arm 301 so that the handle 405 and rigid section 332 will not rotate relative to one another. The handle 405 has a bore 409 through which the threaded shank 401 extends and has flats 410 corresponding to the flats 403 to prevent relative rotation between the shank 401 and the handle 405. A preferred handle 405 has two wings 412 to assist an operator to grip the handle.

A second handle 416 with wings 418 is also provided. The examplary handle 416 has a through aperture 420 extending axially through the handle. The surface defining the aperture 420 has a plurality of longitudinally extending teeth 422 projecting into the aperture 420 which are spaced apart around the aperture, as shown in FIG. 16C. The teeth 422 have generally radially extending surfaces 423 and beveled surfaces 424. The aperture 420 includes an enlarged section forming a shoulder 426. To maintain alignment between the handles 405 and 416, a shaft 428 surrounding the aperture 420 is received within a ring 430 in the handle 405.

A clutch element 432, which may be in the form of a shaft, as seen in FIG. 16A, is provided. It has a through bore 434 through which the threaded shank 401 extends. The upper end 435 of the bore 434 receives a threaded fastener 436. Preferably the fastener 436 is a hex nut and the upper end 435 is correspondingly shaped so the hex nut will be positively rotated with rotation of the clutch element 432. The clutch element 432 is received in the aperture 420 and has a shoulder 438 that engages the shoulder 426 to limit axial movement of the clutch element into the handle 416. The handles 405, 416 also have engaging shoulders 440, 441, respectively, to also limit axial movement of the handles relative to one another. The clutch element 432 has an exterior surface that has teeth 443 like the teeth 422 with radially extending surfaces 444 and beveled surfaces 445. The surfaces 423 and 444 face one another and are positioned to interengage when the handle 416 rotates relative to the clutch element 432 in one direction. This will positively turn or rotate the clutch element 432 with the handle 416. If the threaded shank 401 is a right handed thread, counter-clockwise rotation of the handle 416 will positively turn the fastener 436 to reduce tension in the cable 255.

The beveled surfaces 424, 445 will frictionally interfere with one another when the handle 416 is rotated to rotate the fastener 436 on the shank 401 to shorten and thus tension the cable assembly. The degree of interference between the surfaces 424, 445 will determine the torque required to rotate the handle 416 relative to the clutch element 432. By thus limiting the amount of torque that can be applied to the clutch element 432, the tension in the cable 255 can also be limited. The handle 405 can be grasped by an operator during tightening and loosening of the handle 416 to prevent rotation of the rigid section 332 providing convenience for an operator.

The handles 405, 416 and the clutch element 432 may be made of any appropriate material, preferably, of plastic such as ABS.

Further, a method for selectively isolating and stabilizing cardiac tissue at a surgical site is provided. In operation, the stabilizer is used in heart surgery, including bypass graft surgery as described above. The stabilizer of the present invention is particularly adapted for use in beating heart surgery but may also be used in regular CPB procedures in which the heart is stopped. In all applications, the present invention helps stabilizing the cardiac tissue and retaining it in a desired position or orientation during the procedure. Similarly, the inventive foot and/or some other described novel features of the present invention may be used with heart stabilizer in open-chest surgeries, as well as heart stabilizer adapted for minimally invasive cardiac procedures.

Generally, a method of present invention for stabilizing cardiac tissue at a surgical site includes the following steps:
  obtaining a heart stabilizing device comprising a stabilizing foot having at least two heart engaging bottom surfaces, such bottom surfaces being inwardly angled relative to each other; and placing said angled heart engaging bottom surfaces on opposite sides of the surgical site; applying force to the heart through said angled bottom surfaces to thereby stretch and stabilize the portion of the heart at the surgical site; and finally, performing a medical procedure on the cardiac tissue at a surgical site. While usually the tissue naturally compresses and protrudes between fingers or wings of the foot, the stretching or tension causes the incision at the anastomosis site to spread further open and it also significantly improves the ability of the device to achieve effective stabilization.

An open-chest surgical procedure usually includes first exposing the area of the heart needing surgery. This is done by making an incision on the chest and by splitting the sternum. The spreader 18 is used to hold the sternum separated. The spreader 18 is mounted in the desired location and the heart stabilizer of the present invention may be mounted on such spreader. Adjustment of the position of the arms of the stabilizer is accomplished so that the foot 12 is on the desired area or surgical site on the heart with the fingers 155 positioned on opposite sides of the surgical site with the artery of interest being positioned between the fingers. The assembly connecting the arms and the foot of the present invention allows for a very high adjustability of the device to the specifics of the surgical site. Once the foot of the device is properly positioned, the desired amount of force is applied to the heart at the surgical site and the surgery can commence. If the device is to be used in a non-beating heart procedure, the normal connections to the heart lung bypass equipment must be made and the heart stopped prior to grafting as it is known in the art.

As various changes could be made in the above constructions without departing from the scope of the invention, it is intended that all matter contained in the above description or shown in the accompanying drawings shall be interpreted as illustrative and not in a limiting sense.

What is claimed is:

1. A surgical device for stabilizing cardiac tissue during surgery, said device comprising:
    a support structure having a distal end and a proximal end; and
    a stabilizing foot attached to said support structure at a distal end, the foot comprising two laterally spaced apart fingers connected by a bridge at one end of the fingers, said fingers each having an inner edge with said edges being located generally in a first plane and defining a surgical site therebetween, said fingers having bottom surfaces, each said bottom surface having a beveled surface portion extending upwardly and away from the inner edge at an angle in the range of between about 10° and about 35° from the first plane.

2. The surgical device of claim 1 wherein said inner edges are generally parallel.

3. The surgical device of claim 1 wherein said bottom surfaces each include a second surface portion extending at an angle from the beveled surface to an outer edge of each finger.

4. The surgical device of claim 3 wherein each second surface portion of the bottom surfaces is generally parallel to the first plane.

5. The surgical device as set forth in claim 1 wherein said bottom surfaces are textured.

6. The surgical device as set forth in claim 5 wherein the texture is a plurality of generally concentric ribs.

7. The surgical device of claim 1 further comprising a mounting post for connecting the foot to the support structure.

8. The surgical device of claim 7 wherein the mounting post is secured to the bridge and projects therefrom.

9. The surgical device of claim 7 wherein the mounting post is secured to the finger and projects therefrom.

10. The surgical device as set forth in claim 7 wherein said mounting post is generally normal to said first plane.

11. The surgical device of claim 7 wherein said post is generally parallel to said first plane and generally parallel to a longitudinal axis of each said finger.

12. The surgical device of claim 7 wherein said post is generally parallel to said first plane and generally perpendicular to a longitudinal axis of each said finger.

13. The surgical device of claim 1 wherein said bridge has a bottom surface that has a substantial portion thereof spaced above said first plane.

14. The surgical device of claim 1 wherein said each finger has a top surface that meets the beveled surface portion of the bottom surface of each finger at the corresponding inner edge.

15. The surgical device of claim 14 wherein the top surface of each finger gradually converges with the beveled surface portion of the bottom surface of each finger in the area of the inner edge.

16. The surgical device of claim 1 wherein said beveled surface portion are at least 6 mm wide.

17. The surgical device as set forth in claim 1 wherein said inner edges are spaced apart a distance in the range of between about 6 mm and about 13 mm.

18. The surgical device of claim 7 wherein the mounting post is removably connected to the support structure.

19. The surgical device of claim 18 wherein the connection of the mounting post to the support structure is a snap-fit connection.

20. The surgical device of claim 1 wherein the support structure comprises a first elongate arm and wherein the stabilizing foot is connected to said first elongate arm.

21. The surgical device of claim 20 wherein the stabilizing foot is movably connected to the first elongate arm.

22. The surgical device of claim 21 further comprising a first joint and a first lock means cooperating with the first joint and having a locked position for selective locking of the first arm relative to the stabilizing foot and an unlocked position wherein said first joint is operable to be maintained substantially in position until moved by an operator.

23. The surgical device of claim 20 wherein the support structure further comprises a second elongate arm movably connected to the first elongate arm for selective multi-axis movement of the first and second arms relative to one another.

24. The surgical device of claim 23 further comprising a second joint and a second lock means with a locked position for selective locking of the first and second arms in a selected position relative to one another, and an unlocked position wherein said second joint is operable to maintain said first and second arms substantially in position until moved by an operator.

25. The surgical device of claim 1 wherein the proximal end of the support structure is movably mounted to a surgical spreader.

26. The surgical device of claim 24 further comprising a third joint and a third lock means cooperating with said third joint to removably mount the surgical device to a chest spreader.

27. The surgical device of claim 24 wherein said second joint includes a pair of C-clamps pivotally secured to one another with each said C-clamp having an arm receiving bore therethrough frictionally engaging the respective first or second arm mounted in the respective bore.

28. The surgical device of claim 27 wherein said C-clamps each have a toothed surface in engagement with one another to selectively pivotally lock the C-clamps in a plurality of pivoted positions and the first pivot joint including a fastening member securing the C-clamps together.

29. The surgical device of claim 27 wherein each respective first and second arm can move axially, rotationally and pivotally relative to one another within the C-clamps.

30. The surgical device of claim 26 wherein said first and third lock means include a preload pad.

31. The surgical device as set forth in claim 30 wherein said first and third lock means includes a rod member mounted in the respective arm for selective axial movement therein, one end of the rod is selectively in force applying engagement with the respective preload pad whereby axial movement in a direction toward the respective preload pad will increase the friction and movement in a direction away from the respective preload pad will reduce the friction to as low as the preload friction.

32. A foot for use with a heart stabilizing device for engaging a portion of a heart during a heart surgery procedure, said foot comprising:

two laterally spaced apart fingers, said fingers each having an inner edge with said edges defining a surgical site therebetween, each finger having a bottom surface, each said bottom surface having an angled surface portion extending upwardly and away from the inner edge.

33. The foot of claim 32 wherein an included angle between the angled surface portions is in the range of between about 110° and about 160°.

34. The foot of claim 32 wherein an included angle between the angled surface portions is in the range of between about 120° and about 140°.

35. The foot of claim 32 further comprising a bridge secured to and extending between the fingers adjacent one end of each finger.

36. The foot of claim 33 further comprising a mounting post secured to the bridge or one of the fingers and extending therefrom.

37. The foot of claim 32 wherein said inner edges are generally parallel.

38. The foot of claim 32 wherein said bottom surfaces each include a second surface portion extending at an angle from the angled surface portion to an outer edge of each finger.

39. The foot of claim 38 wherein said second surface portion extends at an angle relative to the respective angled surface portion which is in the range of between about 145° and about 170°.

40. The foot of claim 32 wherein said bottom surface is textured.

41. The foot of claim 40 wherein said texture is a plurality of generally concentric ribs running generally lengthwise of the respective finger.

42. The foot of claim 36 wherein the inner edges of the fingers lie in a first plane and said mounting post is generally normal to said first plane.

43. The foot of claim 36 wherein the inner edges of the fingers lie in a first plane and said mounting post is located at an angle to said first plane.

44. The foot of claim 36 wherein the inner edges of the fingers lie in a first plane and said mounting post is generally parallel to said first plane and generally parallel to a longitudinal axis of each said finger.

45. The foot of claim 36 wherein the inner edges of the fingers lie in a first plane and said mounting post is generally parallel to said first plane and generally perpendicular to a longitudinal axis of each said finger.

46. The foot of claim 35 wherein said bridge has a lower surface that has a substantial portion thereof spaced above a plane defined by the inner edges.

47. The surgical device of claim 32 wherein said each finger has a top surface that meets the angled surface portion of the bottom surface at the corresponding inner edge at an acute angle.

48. The surgical device of claim 32 further comprising a pad removably secured to the bottom surface of the foot.

49. The foot of claim 32 wherein said inner edges are spaced apart a distance in the range of between about 6 m and about 13 mm.

50. The foot of claim 32 wherein the angled surface portion of the bottom surface of each finger has a width of at least about 6 mm.

51. The foot of claim 36 wherein the mounting post is adapted for removable connection of the foot to the heart stabilizing device.

52. The method for selectively isolating and stabilizing cardiac tissue at a surgical site comprising the steps of:

obtaining a device for isolating and stabilizing cardiac tissue comprising a stabilizing foot having at least two heart engaging bottom surfaces, such bottom surfaces being inwardly angled relative to each other;

placing said angled heart engaging bottom surfaces on opposite sides of the surgical site;

applying force to the heart through said angled heart engaging bottom surfaces to thereby stretch and stabilize cardiac tissue at the surgical site;

performing a medical procedure on the cardiac tissue.

53. The method of claim 52 wherein the heart is beating during the medical procedure.

54. The method of claim 52 wherein the force applied through the stabilizing device is a mechanical force.

55. The method of claim 52 wherein the force applied through the stabilizing device is a vacuum force.

56. The method of claim 52 further comprising a step of adjusting the orientation of a stabilizing foot relative to the surgical site.

57. The method of claim 56 wherein the adjusting step further comprises locking the position and orientation of the stabilizing foot relative to the surgical site.

* * * * *